United States Patent
Zablocki et al.

(12)

(10) Patent No.: US 6,642,210 B1
(45) Date of Patent: *Nov. 4, 2003

(54) 2-(N-PYRAZOLO)ADENOSINES WITH APPLICATION AS ADENOSINE $A_{2A}$ RECEPTOR AGONISTS

(75) Inventors: Jeff A. Zablocki, Mountain View, CA (US); Elfatih O. Elzein, Freemont, CA (US); Venkata P. Palle, Sunnyvale, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/018,446

(22) PCT Filed: Jun. 21, 2000

(86) PCT No.: PCT/US00/40281

§ 371 (c)(1),
(2), (4) Date: Apr. 12, 2000

(87) PCT Pub. No.: WO00/78779

PCT Pub. Date: Dec. 28, 2000

Related U.S. Application Data

(63) Continuation-in-part of application No. 09/338,185, filed on Jun. 22, 1999, now Pat. No. 6,403,567.

(51) Int. Cl.[7] .................. A61K 31/70; C07H 19/20; C07H 19/67
(52) U.S. Cl. ............ 514/46; 536/226.3; 536/26.6; 536/27.61; 536/27.62; 536/27.63
(58) Field of Search .............. 514/46, 47; 536/26.3, 536/26.6, 27.61, 27.62, 27.63

(56) References Cited

U.S. PATENT DOCUMENTS

| | | | |
|---|---|---|---|
| 4,956,345 A | 9/1990 | Miyasaka et al. ......... 514/46 |
| 4,968,697 A * | 11/1990 | Hutchison ............... 514/46 |
| 5,070,877 A | 12/1991 | Mohiuddin et al. | |
| 5,189,027 A | 2/1993 | Miyashita et al. ......... 514/46 |
| 5,270,304 A | 12/1993 | Kogi et al. ............. 514/46 |
| 5,459,254 A | 10/1995 | Yamaguchi et al. ..... 536/27.11 |
| 5,593,975 A | 1/1997 | Cristalli .............. 514/46 |
| 5,705,491 A | 1/1998 | Yamada ................ 514/46 |
| 5,770,716 A | 6/1998 | Khan et al. ............ 536/23.1 |
| 5,939,543 A | 8/1999 | Morozumi et al. ....... 536/27.63 |
| 6,403,567 B1 * | 6/2002 | Zablocki et al. ......... 514/46 |

FOREIGN PATENT DOCUMENTS

| | | |
|---|---|---|
| CA | 965411 | 4/1975 |
| EP | 0 354 638 A2 * | 2/1990 |
| JP | Hei 5-9197 | 1/1993 |

OTHER PUBLICATIONS

Marumoto, et al., "Synthesis and Coronary Vasodilating Activity of 2–Substituted Adenosines", *Chem.. Pharm. Bull.* 23(4): 759–774 (1975).

Marumoto, et al., "Synthesis and Enzymatic Activity of Adenosine 3', 5'–Cyclic Phosphate Analogs", *Chem.. Pharm. Bull.* 27(4) 990–1003 (1979).

Persson, et al., "Synthesis and Antiviral Effects of 2–Heteroaryl Substituted Adenosine and 8–Heteroaryl Substituted Adenosine Guanosine Derivatives", *Bioorganic & Medicinal Chemistry*, 3:1377–1382 (1995).

Mager, et al., "Molecular simulation applied to 2–(N'alkylidenehydrazino)–and 2–(N'aralkylidenehydrazino) adenosine $A_2$ Agonists", *Eur J. Med. Chem*, 30:15–25 (1995).

* cited by examiner

*Primary Examiner*—James O. Wilson
*Assistant Examiner*—Lawrence E. Crane
(74) *Attorney, Agent, or Firm*—McDonnell Boehnen Hulbert & Berghoff

(57) ABSTRACT

N-pyrazole substituted 2-adenosine compounds and methods for using the compounds as $A_2A$-adenosine receptor agonists useful to stimulate mammalian coronary vasodilation for therapeutic purposes and as adjuncts in cardiological imaging.

18 Claims, 3 Drawing Sheets

2-(N-PYRAZOLO)ADENOSINES WITH APPLICATION AS ADENOSINE $A_{2A}$ RECEPTOR AGONISTS

This application is a 371 of PCT/US00/40281 filed Jun 21, 2000 which is a continuation in part of Ser. No. 09/338,185, filed Jun. 22, 1999 now U.S. Pat. No. 6,403,567.

BACKGROUND OF THE INVENTION

1. Field of Invention

This invention includes N-pyrazole substituted 2-adenosine compounds that are useful as $A_{2A}$ receptor agonists. The compounds of this invention are vasodilating agents that are useful as heart imaging aids that aid in the identification of mammals, and especially humans who are suffering from coronary disorders such poor coronary perfusion which is indicative of coronary artery disease (CAD). The compounds of this invention can also be used as therapeutics for coronary artery disease as well as any other disorders mediated by the $A_{2A}$ receptor.

2. Description of the Art

Pharmacological stress is frequently induced with adenosine or dipyridamole in patients with suspected CAD before imaging with Tl scintigraphy or echocardiography. Both drugs effect dilation of the coronary resistance vessels by activation of cell surface $A_2$ receptors. Although pharmacological stress was originally introduced as a mean of provoking coronary dilation in patients unable to exercise, several studies have shown that the prognostic value of $^{201}$Tl or echocardiographic imaging in patients subjected to pharmacological stress with adenosine or dipyridamole was equivalent to patients subjected to traditional exercise stress tests. However, there is a high incidence of drug-related adverse side effects during pharmacological stress imaging with these drugs such as headache and nausea, that could be improved with new therapeutic agents.

Adenosine $A_{2B}$ and A3 receptors are involved in a mast cell degranulation and, therefore, asthmatics are not give the non-specific adenosine agonists to induce a pharmacological stress test. Additionally, adenosine stimulation of the $A_1$ receptor in the atrium and A-V node will diminish the S-H interval which can induce AV block (N. C. Gupto et al.; *J. Am Coll. Cardiol*; (1992) 19: 248–257). Also, stimulation of the adenosine $A_1$ receptor by adenosine may be responsible for the nausea since the Al receptor is found in the intestinal tract (J. Nicholls et al.; *Eur. J. Pharm.* (1997) 338(2) 143–150).

Animal data suggests that specific adenosine $A_{2A}$ subtype receptors on coronary resistance vessels mediate the coronary dilatory responses to adenosine, whereas subtype $A_{2B}$ receptor stimulation relaxes peripheral vessels (note: the latter lowers systemic blood pressure). As a result there is a need for pharmaceutical compositions that are $A_{2A}$ receptor agonists that have no pharmacological effect as a result of stimulating the $A_1$ receptor in vivo. Furthermore, there is a need for $A_{2A}$ receptor agonists that have a short half-life, and that are well tolerated by patients undergoing pharmacological coronary stress evaluations.

SUMMARY OF THE INVENTION

In one aspect, this invention includes 2-adenosine N-pyrazole compounds that are useful $A_{2A}$ receptor agonists.

In another aspect, this invention includes pharmaceutical compounds including 2-adenosine N-pyrazole that are well tolerated with few side effects.

Still another aspect of this invention are N-pyrazole compounds that can be easily used in conjunction with radioactive imaging agents to facilitate coronary imaging.

In one embodiment, this invention includes 2-adenosine N-pyrazole compounds having the following formula:

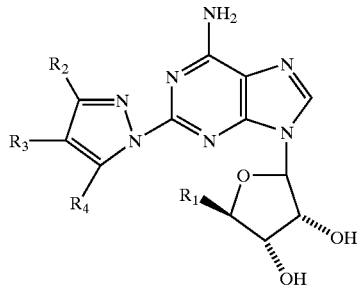

In another embodiment, this invention includes methods for using compounds of this invention to stimulate coronary vasodilatation in mammals, and especially in humans, for stressing the heart induced steal situation for purposes of imaging the heart In still another embodiment, this invention is a pharmaceutical composition comprising one or more compounds of this invention and one or more pharmaceutical excipients.

DESCRIPTION OF THE FIGURES

In FIG. 1B, the bars represent mean±SEM of single measurement from 6 rat isolated perfused hearts;

DESCRIPTION OF THE CURRENT EMBODIMENT

Figure 1A:
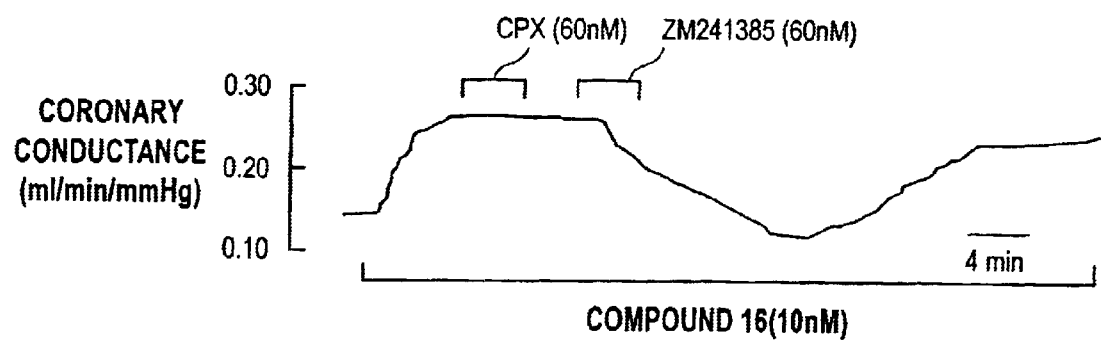
FIG 1A is a analog record of the increase in coronary conductance caused by Compound 16 of this invention before and after infusions of CPX and ZM241385.

This invention includes a class of 2-adenosine N-pyrazole having the formula:

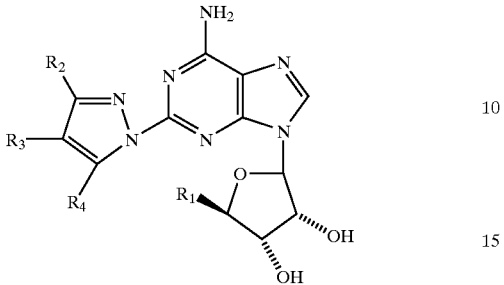

wherein $R^1 = CH_2OH$, $—CONR_5R_6$;

$R^3$ is independently selected from the group consisting of $C_{1-15}$ alkyl, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R_{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $COR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$, $—CONR^7R^8$, $C_{2-15}$ alkenyl, $C_{2-15}$ alkynyl, heterocyclyl, aryl, and heteroaryl, wherein the alkyl, alkenyl, alkynyl, aryl, heterocyclyl and heteroaryl substituents are optionally substituted with from 1 to 3 substituents independently selected from the group consisting of halo, alkyl, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R_{20})_2$ $NR^{20}COR^{22}$, $NR^{20}CO_2^{22}$, $NR^{20}CON(R_{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}COR^{22}$, $OCONR^{20}SO_2R^{22}$, $OC(O)R^{20}$, $C(O)OCH_2OC(O)R^{20}$, and $OCON(R^{20})_2$ and wherein the optional substituted heteroaryl, aryl, and heterocyclyl substituents are optionally substituted with halo, $NO_2$, alkyl, CF3, amino, mono- or di- alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^5$ and $R^6$ are each individually selected from H, and $C_1-C_{15}$ alkyl that is optionally substituted with from 1 to 2 substituents independently selected from the group of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}$, $COR^{22}$, $SO_2NR^{20}C_2R^{22}$, $SO_2NR^{20}CON(R^{20})_2$, $N(R^{20})_2$, $NR^{20}COR^{22}$, $NR^{20}CO_2R^{22}$, $NR^{20}CON(R^2)_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^2)_2$ wherein each optional substituted heteroaryl, aryl, and heterocyclyl substituent is optionally substituted with halo, $NO_2$, alkyl, $CF_3$, amino, monoalkylamino, dialkylamino, alkylarnide, arylamide, heteroarylamide, $NCOR^{22}$, $NR^{20}SO_2R^{22}$, $COR^{20}$, $CO^2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^7$ is selected from the group consisting of hydrogen, $C_{1-15}$ alkyl, $C_{2-15}$ alkenyl, $C_{2-15}$ alkynyl, heterocyclyl, aryl and heteroaryl, wherein the alkyl alkenyl, alkynyl, aryl, heterocyclyl and heteroaryl substituents are optionally substituted with from 1 to 3 substituents independently selected from the group of halo, $NO_2$, heterocyclyl aryl, heteroaryl, $CF_3$, CN, $OR^{20}$, $SR^{20}$, $N(R^{20})_2$ $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R20)_2$ $NR^{20}COR^{22}$, $NR^{20}C_2R^{22}$, $NR^{20}CON(R^{20})_2$, $NR^{20}C(NR^{20})NHR^{23}$, $COR^{20}$, $CO_2R^{20}$, $CON(R20)_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$ and $OCON(R^{20})_2$ and wherein each optional substituted heteroaryl, aryl and heterocyclyl substituent is optionally substituted with halo, $NO_2$, alkyl, $CF_3$, amino, mono- or di- alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^8$ is selected from the group consisting of hydrogen, $C_{1-15}$ alkyl, $C_{2-15}$ alkenyl, $C_{2-15}$ alkynyl, heterocyclyl, aryl, and heteroaryl wherein the alkyl alkenyl, alkynyl, aryl heterocyclyl, and hetemaryl substituents are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^2)_2$, $S(O)R^{22}$, $SO_2R^{22}$, $SO_2N(R^{20})_2$, $SO_2NR^{20}COR_{22}$, $SO_2NR^{20}CO_2R^{22}$ $SO_2NR^{20}CON(R_{20})_2$, $N(R^{20})_2$ $NR_{20}COR^{22}$, $NR^{20}CO_2R^{22}$, $NR^{20}CON_{20}(R^{20})_2$, $SO_2NR^{20}CO_2R^{22}$, $OCONR^{20}SO_2R^{22}$, $OC(O)R^{20}$, $C(O)OCH_2OC(O)R^{20}$ and $OCON(R^{20})_2$ and wherein each optional substituted heteroaryl, aryl, and heterocyclyl substituent is optionally substituted with halo, $NO_2$, alkyl, $CF_3$, amino, mono- or di- alkylamino, alkyl or aryl or heteroaryl amide, $NCOR^{22}$, $NR^{20}SO_2R^2$, $COR^{20}$, $CO_2R^{20}$, $CON(R^{20}_{20})$, $NR^{20}$ $CON(R^{20}CON(R^{20})_2$, $OC(O)R^{20}$, $OC(O)N(R^2)_2$, $SR^{20}$, $S(O)R^{22}$, $SO_2R^{22}$, $SO_2N(R^{20})_2$, CN, and $OR^{20}$;

$R^8$ is selected from the group consisting of H, $C_{1-15}$ alkyl, $C_{2-15}$ alkenyl, $C_{2-15}$ alkynyl, heterocyclyl, aryl, and heteroaryl, wherein the alkyl alkenyl, alkynyl, heterocyclyl, aryl, and heteroaryl substituents are optionally substituted with from 1 to 3 substituents independently selected from the group consisting of halo, $NO_2$, heterocyclyl, aryl, heteroyl, $CF_3$, CN, $OR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{290}$, $COR^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional susbtituted hetereoaryl, aryl and heterocyclyl sustitutet is optionally sustitutd with halo, $NO^2$, alkyl, $CF_3$, amino- or di-alkylamino, alkyl or aryl or heteroaryl amide, $NCOR^{22}$, $NR^{20}SO_2R^{22}$, $COR^{20}$, $CO_2R^{20}$, $CON(R^{20})_2 NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl sustituents are optionally substituted with from 1 to 3 substituents independently selected from halo, alkyl, mono- or dialkylamino, alkyl or aryl or heteroaryl amide, CN, O—$C_{1-6}$, alkyl, $CF_3$, aryl, and heteroaryl;

$R^{22}$ is selected from the group consisting of $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl mono- or dialkylamino, alkyl or aryl or heteroaryl amide, CN, O—$C_{1-6}$ alkyl, $CF_3$, aryl, and heteroaryl; and wherein $R^2$ and $R^4$ are selected from the group consisting of H, $C_{1-15\,6}$ alkyl and aryl, wherein the alkyl and aryl substituents are optionally substituted with halo, CN, $CF_3$, $OR^{20}$ and $N(R^{20})_2$ with the proviso that when $R^2$ is not hydrogen then $R^4$ is hydrogen, and when $R^4$ is not hydrogen then $R^2$ is hydrogen.

In preferred compounds of this invention, $R^3$ is selected from the group consisting of $C_{1-15}$ alkyl, halo, $CF_3$, CN, $OR^{20}$, $SR^{20}$, $S(O)R^{22}$, $SO_2R^{22}$, $SO_2N(R^{22})_2$, $COR^{20}$, $CO_2R^{20}$, —$CONR^7R^8$, aryl and heteroaryl wherein the alkyl, aryl and heteroaryl substituents are optionally substituted with from 1 to 3 substituents independently selected from the group consisting of halo, aryl, heteroaryl, CF3, CN, $OR^{20}$, $SR^{20}$, $S(O)R^{22}$, $SO_2R^{22}$, $SO_2N(R^{20})_2$, $COR^{20}$, $CO_2R^{20}$ or $CON(Rn_{20})_2$, and each optional heteroaryl and aryl substituent is optionally substituted with halo, alkyl, $CF_3$ CN, and $OR^{20}$; $R^5$ and $R^6$ are independently selected from the group of H and $C_{1-15}$ alkyl including one optional aryl substituent and each optional aryl substituent that is optionally substituted with halo or CF3; R7 is selected from the group consisting of $C_{1-15}$ alkyl, $C_{2-15}$ alkynyl, aryl, and heteroaryl, wherein the alkyl, alkynyl aryl, and heteroaryl substituents are optionally substituted with from 1 to 3 substituents independently selected from the group consisting of halo, aryl, heteroaryl, $CF_3$, CN, $OR^{20}$, and each optional heteroaryl and aryl substituent is optionally substituted with halo, alkyl, $CF_3$ CN, or $OR^{20}$; $R^8$ is selected from the group consisting of hydrogen and $C_{1-15}$ alkyl; $R^{20}$ is selected from the group consisting of H, $C_{1-4}$, alkyl and aryl, wherein alkyl and aryl substituents are optionally substituted with one alkyl substituent; and $R^{22}$ is selected from the group consisting of H, $C_{1-4}$ alkyl and aryl which are each optionally substituted with from 1 to 3 alkyl group.

In more preferred compounds, $R^1$ is $CH_2OH$; $R^3$ is selected from the group consisting of $CO_2R^{20}$, —$CONR^7R^8$ and aryl where the aryl substituent is optionally substituted with from 1 to 2 substituents independently selected from the group consisting of halo, $C_{1-4}$ alkyl, $CF_3$ and $OR^{20}$; $R^7$ is selected from the group consisting of hydrogen, $C_{1-8}$ alkyl and aryl, where the alkyl and aryl substituents are optionally substituted with one substituent selected from the group consisting of halo, aryl, $CF_3$, CN, O $R^{20}$ and wherein each optional aryl substituent is optionally substituted with halo, alkyl, $CF_3$ CN, and $OR^{20}$; $R^8$ is selected from the group consisting of hydrogen and $C_{1-8}$ alkyl; and $R^{20}$ is selected from hydrogen and $C_{1-4}$ alkyl.

In a still more preferred embodiment, $R^1$=$CH_2OH$; $R^3$ is selected from the group consisting of $CO_2R^{20}$, —$CONR^7R^8$, and aryl that is optionally substituted with one substituent selected from the group consisting of halo, $C_{1-3}$ alkyl and $OR^{20}$; $R^7$ is selected from of hydrogen, and $C^{1-3}$ alkyl; $R^8$ is hydrogen; and $R^{20}$ is selected from hydrogen and $C_{1-4}$ alkyl. In this preferred embodiment, $R^3$ is most preferably selected from —$CO_2Et$ and —CONHEt.

In another still more preferred embodiment, $R^1$=—CONHEt, $R^3$ is selected from the group consisting of $CO_2R^{20}$, —$CONR^7R^8$, and aryl in that aryl is optionally substituted with from 1 to 2 substituents independently selected from the group consisting of halo, $C_{1-3}$ alkyl, $CF_3$ or $OR^{20}$; $R^7$ is selected from the group consisting of hydrogen, and $C_{1-8}$ alkyl that is optionally substituted with one substituent selected from the group consisting of halo, $CF_3$, CN or $OR^{20}$; $R^8$ is selected from the group consisting of hydrogen and $C^{1-3}$ alkyl; and $R^{20}$ is selected from the group consisting of hydrogen and $C^{1-4}$ alkyl. In this more preferred embodiment, $R^8$ is preferably hydrogen, $R^7$ is preferably selected from the group consisting of hydrogen, and $C^{1-3}$, and $R^{20}$ is preferably selected from the group consisting of hydrogen and $C_{1-4}$ alkyl.

In a most preferred embodiment, the compound of this invention is selected from ethyl1-{9-[(4S,2R,3R,5R)-3,4-dihydroxy-5-(hydroxymethyl)oxolan-2-yl]-6-aminopurin-2-yl}pyrazole-4-carboxylate, (4S,2R,3R,5R)-2-{6-amino-2-[4(-4-chlorophenyl pyrazolyl]purin-9-yl}-5-(hydroxymethyl) oxolane-3,4-diol, (4S,2R,3R,5R)-2-{6-amino-2-[4(4-methoxyphenyl)pyrazolyl]purin-9-yl}-5-(hydroxymethyl) oxolane-3,4-diol, (4S,2R,3R,5R)-2-{6-amino-2-[4-(4-methylphenyl)pyrazolyl]purin-9-yl}-5-(hydroxymethyl) oxolane-3,4-diol, (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, 1-{9-[(4S,2R,3R,5R)-3,4-dihydroxy-5-(hydroxymethyl)oxolan-2-yl]-6-aminopurin-2-yl}pyrazole-4carboxylic acid, (1-{9-[(4S,2R,3R,5R)-3,4-dihydroxy-5-(hydroxymethyl)oxolan-2-yl]-6-aminopurin-2-yl}pyrazol-4-yl)-N,N-dimethylcarboxamide, (1-{9-[(4S,2R,3R,5R)-3,4-dihydroxy-5-(hydroxymethyl)oxolan-2-yl]-6-aminopurin-2-yl}pyrazol-4-yl)-N-ethylcarboxamide, 1-{9-[(4S,2R,3R,5R-3,4-dihydroxy-5-(hydroxymethyl)oxolan-2-yl]-6-aminopurin-2-yl}pyrazole-4-carboxamide, 1-{9-[(4S,2R,3R,5R)-3,4-dihydroxy-5-(hydroxymethyl)oxolan-2-yl]-6-aminopurin-2-yl}pyrazol-4-yl)-N-(cyclopentylmethyl) carboxamide, (1-{9-[(4S,2R, 3R,5R)-3,4-dihydroxy-5-hydroxymethyl)oxolan-2-yl]-6-aminopurin-2-yl}pyrazol-4-yl)-N-[(4-chlorophenyl)methyl]carboxamide, Ethyl 2-[(1-{9-[(4S,2R,3R,5R)-3,4-dihydroxy-5-(hydroxymethyl) oxolan-2-yl]-6-aminopurin-2-yl}pyrazol-4-yl) carbonylamino]acetate, and mixtures thereof.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically de fined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloallyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—lone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—lone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcabonylamino, or the like attached at any available point to produce a stable compound.

"Alkyl alkenyl" refers to a group —R—CR'=CR''' R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably. 5–6, ring members and/or optionally substituted with 1 to 3 groups or substituents of halo, hydroxy, alkoxy, alkylthio, alkylsuifinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—lone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups aminosulfonyl optionally N-mono- or N,N-disubstituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulkily, sulfonyl and N-oxide of a tertiary ring nitrogen. A carbon or nitrogen atom is the point of attachment of the heteroaryl ring structure such that a stable aromatic ring is retained. Examples of heteroaryl groups are pyridnyl, pyridazinyl, pyrazinyl, quinazolinyl, purinyl, indolyl, quinolinyl, pyrpmdinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofulranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in Schemes 1–4. Compounds having the general formula IV can be prepared as shown in Scheme 1.

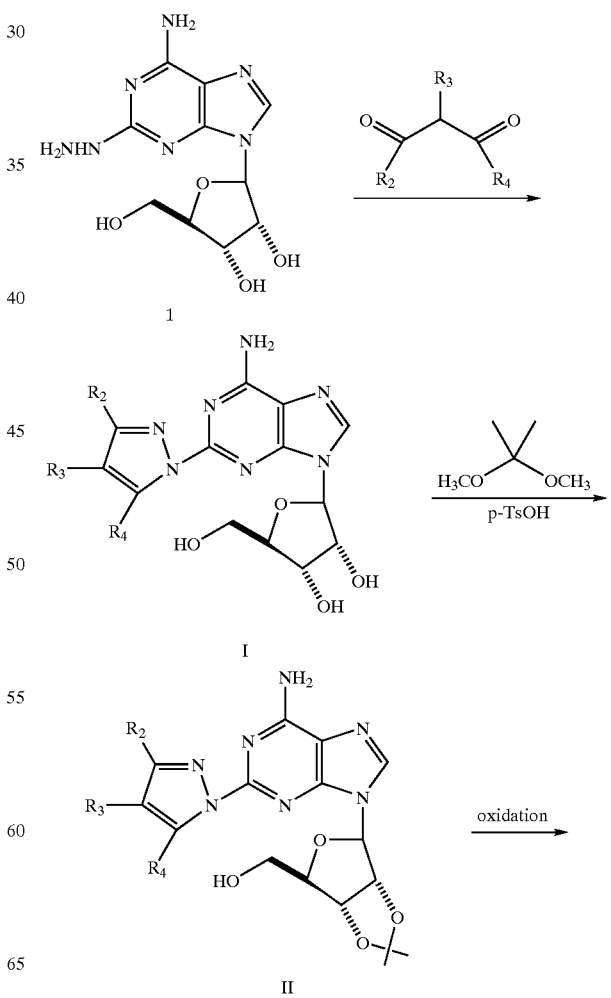

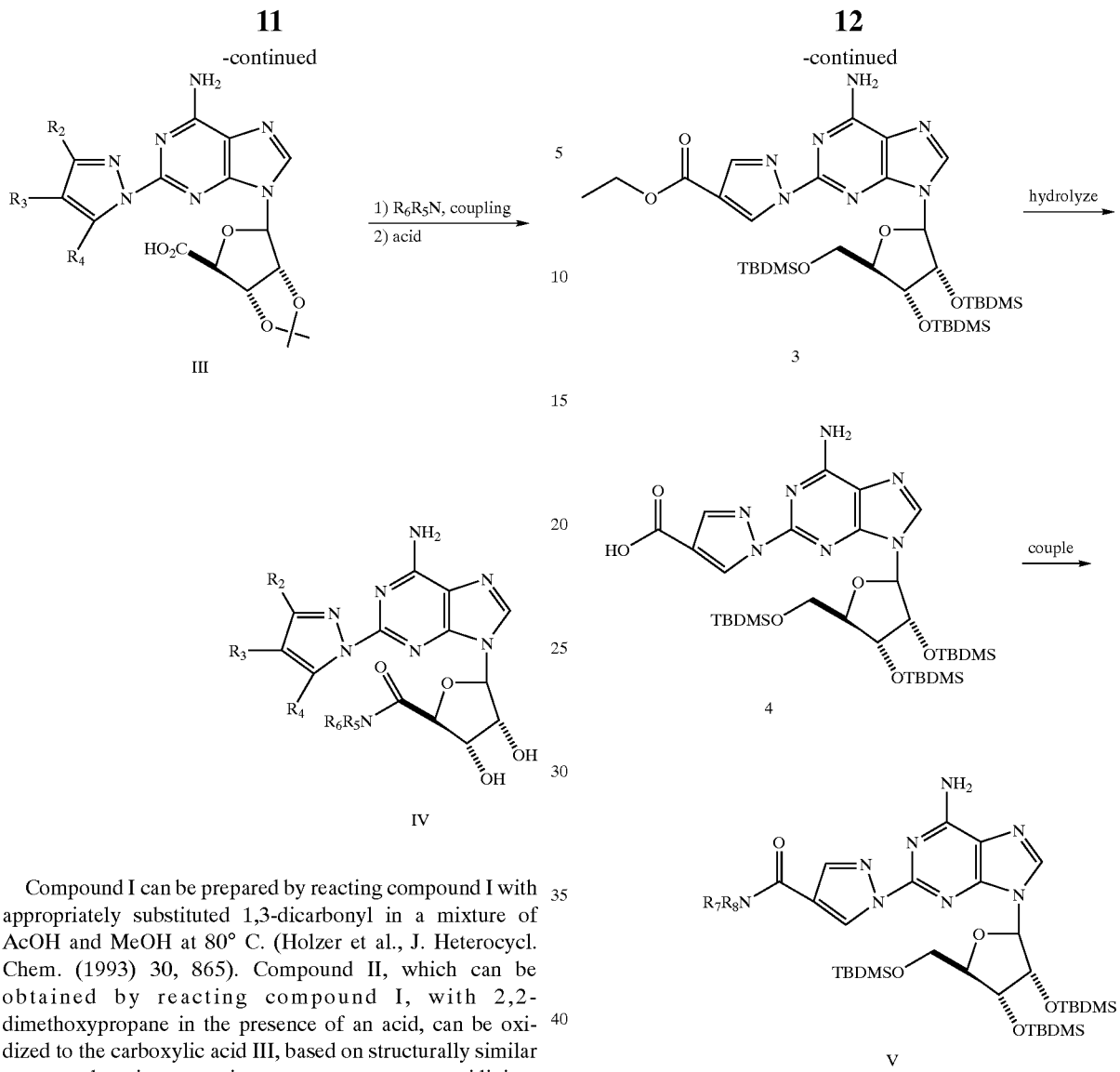

Compound I can be prepared by reacting compound I with appropriately substituted 1,3-dicarbonyl in a mixture of AcOH and MeOH at 80° C. (Holzer et al., J. Heterocycl. Chem. (1993) 30, 865). Compound II, which can be obtained by reacting compound I, with 2,2-dimethoxypropane in the presence of an acid, can be oxidized to the carboxylic acid III, based on structurally similar compounds using potassium permanganate or pyridinium chlorocbromate (M. Hudlicky, (1990) Oxidations in Organic Cherity ACS Monographs, American Chemical Society, Washington D.C.). Reaction of a primary or secondary amine having the formula $HNR^6R^7$, and compound MI using DCC (M. Fujino et al., Chem. Pharm. Bull. (1974), $22,1$i857), PyBOP (J. Martinez et al., J. Med. Chem. (1988) 28, 1874) or PyBrop (3. Caste et al. Tetrahedron, (1991), 32, 1967) couplings conditions can afford compound IV.

Compound V can be prepared as shown in Scheme 2. The Tri TBDMS derivative 4 can be obtained by treating compound 2 with TBDMSCl and imidazole in DMF followed by hydrolysis of the ethyl ester using NaOH. Reaction of a primary or secondary amine with the formula $HNR^6R^7$, and compound 4 using DCC (M. Fujino et al., Chem. Pharm. Bull. (1974), 22, 1857), PyBOP (J. Martinez et al., J. Med. Chem. (1988) 28, 1874) or PyBrop (J. Caste et al. Tetrahedron, (1991), 32, 1967) coupling conditions can afford compound V.

Scheme 2.

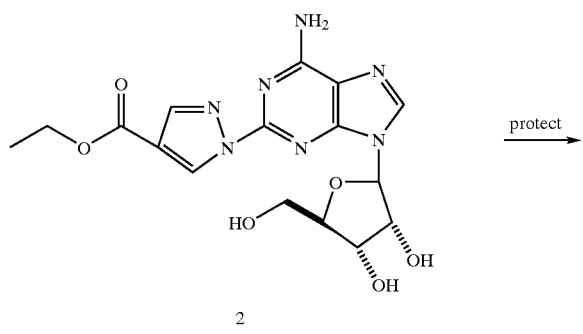

Scheme 3

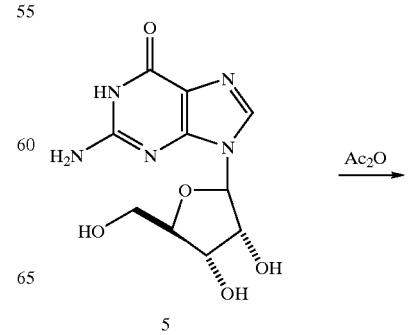

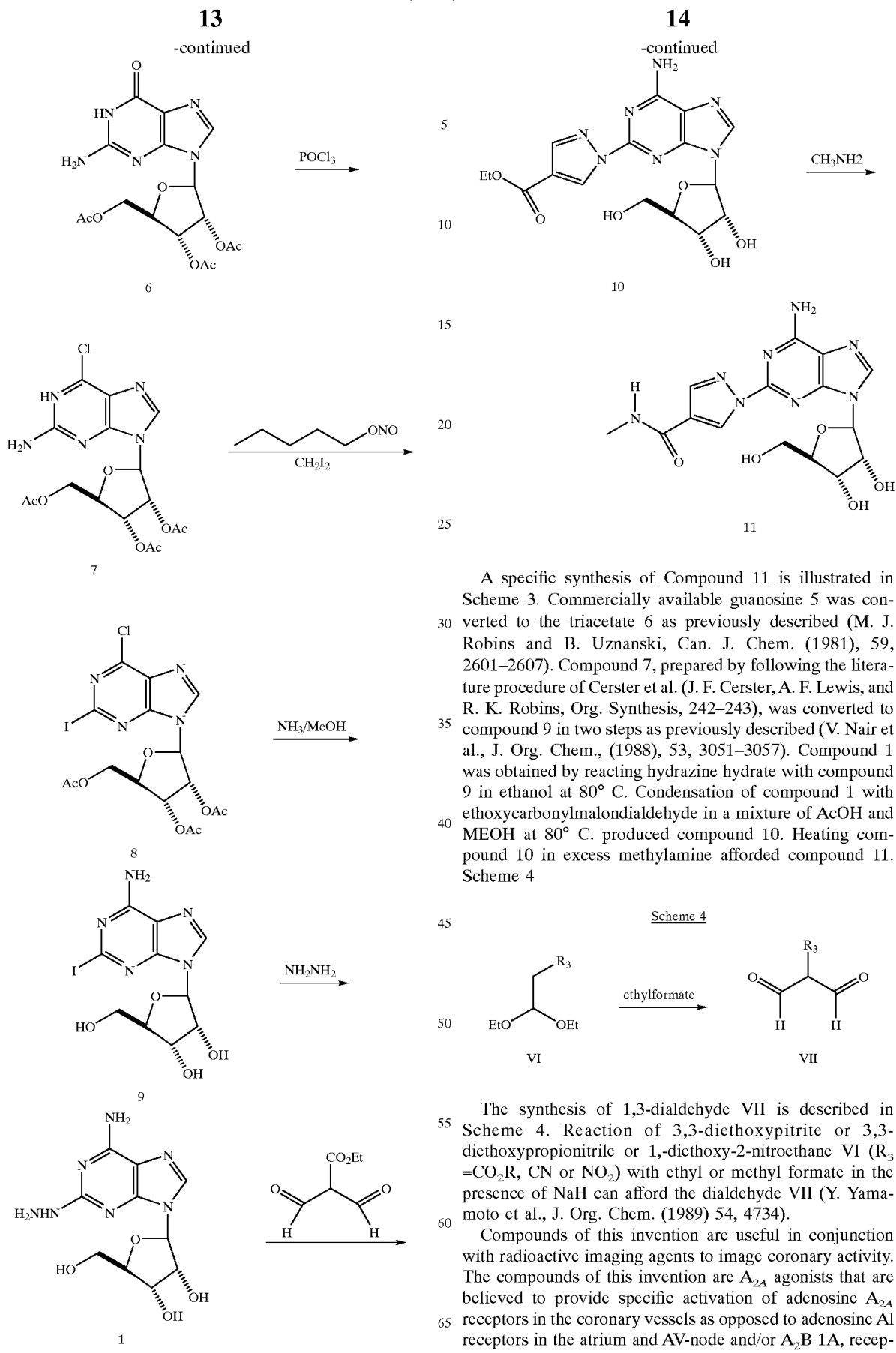

A specific synthesis of Compound 11 is illustrated in Scheme 3. Commercially available guanosine 5 was converted to the triacetate 6 as previously described (M. J. Robins and B. Uznanski, Can. J. Chem. (1981), 59, 2601–2607). Compound 7, prepared by following the literature procedure of Cerster et al. (J. F. Cerster, A. F. Lewis, and R. K. Robins, Org. Synthesis, 242–243), was converted to compound 9 in two steps as previously described (V. Nair et al., J. Org. Chem., (1988), 53, 3051–3057). Compound 1 was obtained by reacting hydrazine hydrate with compound 9 in ethanol at 80° C. Condensation of compound 1 with ethoxycarbonylmalondialdehyde in a mixture of AcOH and MEOH at 80° C. produced compound 10. Heating compound 10 in excess methylamine afforded compound 11.

Scheme 4

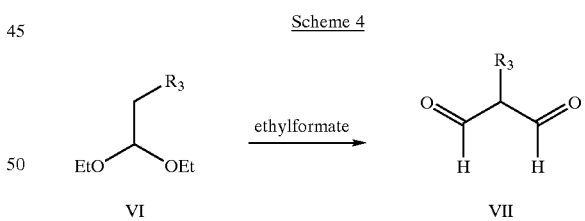

The synthesis of 1,3-dialdehyde VII is described in Scheme 4. Reaction of 3,3-diethoxypitrite or 3,3-diethoxypropionitrile or 1,-diethoxy-2-nitroethane VI ($R_3$ =$CO_2R$, CN or $NO_2$) with ethyl or methyl formate in the presence of NaH can afford the dialdehyde VII (Y. Yamamoto et al., J. Org. Chem. (1989) 54, 4734).

Compounds of this invention are useful in conjunction with radioactive imaging agents to image coronary activity. The compounds of this invention are $A_{2A}$ agonists that are believed to provide specific activation of adenosine $A_{2A}$ receptors in the coronary vessels as opposed to adenosine Al receptors in the atrium and AV-node and/or $A_2B$ 1A, receptors in peripheral vessels, thus avoiding undesirable side-effects. Upon administration in a therapeutic amount, the compounds of this invention cause coronary blood vessels to vasodilate to induce coronary steal wherein healthy coronary vessels steal blood from unhealthy vessels resulting in lack of blood flow to heart tissues. Lower doses of the $A_{2A}$ agonists may provide beneficial coronary vasodilatation (less severe) in the treatment of chronic CAD.

As $A_{2A}$ agonists, the compounds of this invention are also useful in adjunctive therapy with angioplasty to induce dilation, inhibit platelet aggregation, and as a general anti-inflammatory agent. $A_{2A}$ agonists, such as the compounds of this invention, can provide the therapeutic benefits described above by preventing neutrophil activation (Purinergic Approaches in Experimental Therapeutics K. A. Jacobson and M. F. Jarvis 1997 Wiley, New York). The compounds of this invention are also effective against a condition called no-reflow in which platelets and neutrophils aggregate and block a vessel. As $A_{2A}$ 1A, agonists, the compounds of this invention are effective against no-reflow by preventing neutrophil and platelet activation (e.g., they are believed to prevent release of superoxide from neutrophils). As $A_{2A}$ agonists, the compounds of this invention are also useful as cardioprotective agents through their anti-inflammatory action on neutrophils. Thus, in situations when the heart will go through an ischemic state such as a transplant, they will be useful.

This invention also includes pro-drugs of the above-identified $A_{2A}$ agonists. A pro-drug is a drug which has been chemically modified and may be biological inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbonate derivatives which may be cleaved by esterases or lipases, for example; (2) peptides which may be recognized by specific or non specific proteinase; or (3) derivatives that accumulate at a site of action through membrane selection or a pro-drug form or modified pro-drug form, or any combination of (1) to (3) above.

The compounds may be administered orally, intravenously, through the epidermis or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. This dose is typically administered in a solution about 5 minutes to about an hour or more prior to coronary imaging. No unacceptable toxicological effects are expected when compounds of the invention are administered in accordance with the present invention.

If the final compound of this invention contains a basic group, an acid addition salt may be prepared Acid addition salts of the compounds are prepared in a standard manner in a suitable solvent from the parent compound and an excess of acid, such as hydrochloric, hydrobromic, sulfuinc, phosphoric, acetic, maleic, succinic, or methanesulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^{+}$, are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule. It is preferred that the compositions of this invention are administered as a solution either orally or intravenously by continues infusion or bolus.

The Examples which follow serve to illustrate this invention. The Examples are intended to in noway limit the scope of this invention, but are provided to show how to make and use the compounds of this invention. In the Examples, all temperatures are in degrees Centigrade.

EXAMPLE 1

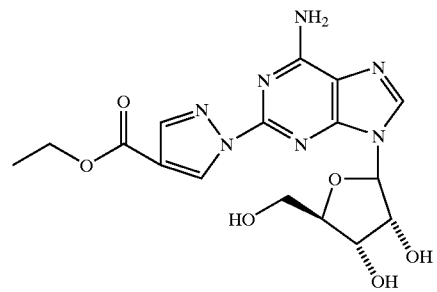

Ethyl1-{9-[(4S,2R,3R,5R)-3,4-dihydroxy-5-(hydroxymethyl)oxolan-2-yl]-6-aminopurin-2-yl}pyrazole-4-carboxylate (12)

To a suspension of 2-hydrazinoadenosine (0.025 g, 0.08 mmol) in a 1:1 mixture of MeOH/AcOH was added (ethoxycarbonyl)malondialdehyde ((0.019 g, 0.12 mmol) and the mixture was heated heated at 80° C. for 3 h. The precipitate formed was collected by filtration and washed with EtOH and ether to afford 12. ¹HNMR (DMSO-d6) δ 1.25 (t, 3H), 3.5 (m, 1 H), 3.6 (m, 1H), 3.8 (d, 1H), 4.15 (d, 1H), 4.55 (m, 1H), 5.0 (t, 1H), 5.2 (d, 1H), 5.5 (d, 1H), 5.5 (d, 1H), 5.9 (d, 1H), 7.15–7.3 (m, 5H), 7.8 (br s, 2H), 8.1 (s, 1H), 8.4 (s, 1H,) 8,9(s, 1H).

EXAMPLE 2

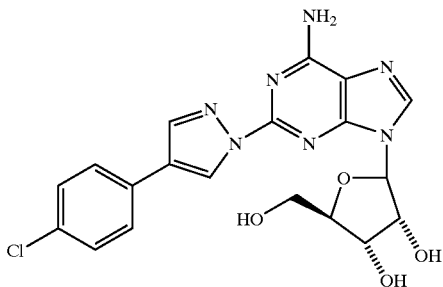

(4S,2R,3R,5R)-2-{-Amino-2-[4-(4-chlorophenyl) pyrazolyl]purin-9-yl}-5-(hydroxymethyl)oxolane-3, 4-diol (13)

To a suspension of 2-hydrazinoadenosine (0.025 g, 0.08 mmol) in a 1:1 mixture of MeOH/AcOH was added 2-(4-chloro)phenylmalondialdehyde (0.022g, 0.12 mmol) and the mixture was heated at 80° C. for 3 h. The precipitate formed was collected by filtration and washed with EtOH and Ether to afford 13. ¹HNMR (DMSO-d6) δ 3.5 (m, 1H), 3.6 (m, 1H), 3.8 (d, 1H), 4.15 (d, 1H), 4.2 (q, 2H), 4.55 (m, 1H), 5.9 (d, 1H), 7.45 (d, 2H), 7.75 (d, 2H)8.25 (s, 1H), 8.35 (s, 1H), 8.9 (s, 1H).

EXAMPLE 3

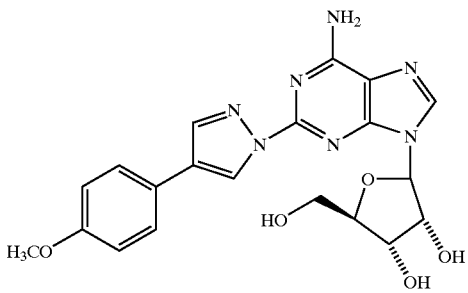

(4S,2R,3R,5R)-2-{6-Amino-2-[4-(4-metboxyphenyl) pyrazolyl]purin-9-yl}-5-(hydroxymethyl)oxolane-3, 4-diol (14)

To a suspension of 2-hydrazinoadenosine (0.025 g, 0.08 mmol) in a 1:1 mixture of MeOH/AcOH was added 2-(4-methoxy)phenylmalondialdehyde (0.022g, 0.12 mmol) and the mixture was heated at 80° C. for 3 h. The precipitate formed was collected by filtration and washed with EtOH and Ether to afford 14. ¹HNMR (DMSO-d6) δ 3.55 (m, 1H), 3.65 (m, 1 H), 3.75 (s, 3H), 3.9 (d, 1H), 4.15 (d, 1H), 4.6 (m, 1H), 5.9 (d, 1H), 6.75 (d, 2H), 7.6 (d, 2H),8.15 (s, 1H), 8.35 (s, 1H), 8.8 (s, 1H).

EXAMPLE 4

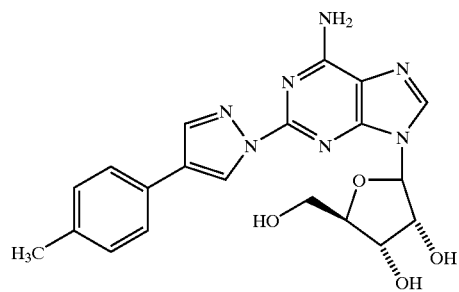

(4S,2R,3R,5R)-2-{6-Amino2-[4-(4-methylphenyl) pyrazolyl]purin-9-yl}-5-(hydroxymethyl)oxolane-3, 4-diol (15)

To a suspension of 2-hydrazinoadenosine (0.025 g, 0.08 mmol) in a 1:1 mixture of MeOH/AcOH was added 2-(4-methyl)phenylmalondialdehyde (0.019 g, 0.12 mmol) and the mixture was heated at 80° C. for 3 h. The precipitate formed was collected by filtration and washed with EtOH and Ether to afford 15. ¹HNMR (DMSO-d6) δ 3.55 (m, 1H\), 3.65 (m, 1H), 3.75 (s, 3H), 3.9 (d, 1H), 4.15 (d, 1H), 4.6 (m, 1H), 5.9 (d, 1H), 6.75 (d, 2H), 8.15 (s, 1H), 8.35 (s, 1H), 8.8 (s, 1H).

EXAMPLE 5

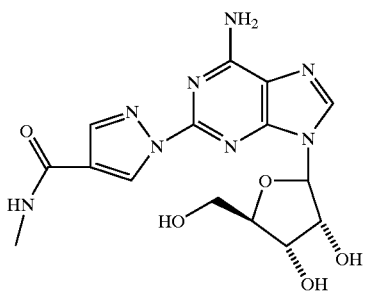

(1-{9-[(4S,2R,3R,-5R)-3,4-dihydroxy-5-(bydroxymethyl)oxolan-2-yl]-6-aminopurin-2-yl}pyrazol-4-yl)-N-methylcarboxamide (16)

Compound 12 (0.05 mg, 0.12 mmol) was added to 4 mL methylamine (40% sol. In water). The mixture heated at 65° C. in for 24 h. After concentration in vacuo, the residue was purified using prep. TLC (10% MeOH:DCM). ¹HNMR (CD₃OD) δ 2.90 (s, 3H), 3.78 (m, 1H), 3.91 (m, 1H), 4.13 (d, 1H), 4.34 (d, 1H), 4.64 (m, 1H), 6.06 (d, 1H), 8.38 (s, 1H), 9.05 (s, 1H).

EXAMPLE 6

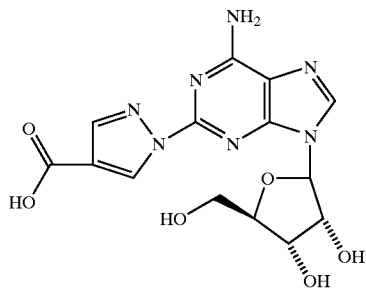

1-{9-[(4S,2R,3R,5R)-3,4-dihydroxy-5-(hydroxymethyl)oxolan-2-yl]-6-aminopurin-2-yl}pyrazole-4-carboxylic Acid (17)

Compound 12 (0.05 mg, 0.12 mmol) was dissolved one equivalent of 1N NaOH. The solution was allowed to stir at Rt for 2 h, then acidified to pH 4. The resulting precipitate was filtered and washed with water and ether. $^1$HNMR (CD$_3$OD) Δ3.75 (m, 1H), 3.90 (m, 1H), 4.13 (d, 1H), 4.43 (d, 1H), 4.64 (m, 1H), 6.05 (d, 1H), 8.10 (s, 1H), 8.35 (s, 1H), 9.05 (s, 1H).

EXAMPLE 7

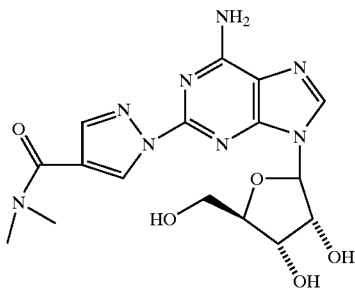

(1-{9-[(4S,2R,3R,5R)-3,4-dihydroxy-5-(hydroxymethyl)oxolan-2-yl]-6-aminopurin-2-yl}pyrazol-4-yl)-N,N-dimethylcarboxamide (18)

Compound 18 was prepared in a manner similar to that of compound 16 using dimethylamine instead of methylamine, MS 405.12 (M+1).

EXAMPLE 8

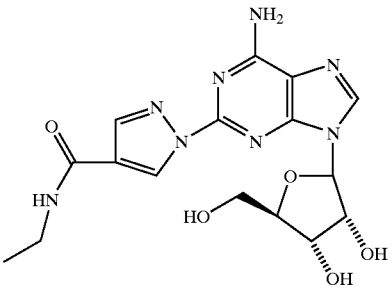

(1-{9-[(4S,2R,3R,5R)-3,4-dihydroxy-5-(hydrozymethyl)oxolan-2-yl]-6-aminopurin-2-yl}pyrazol-4-yl)-N-ethylcarboxamide (19)

Compound 19 was prepared in a manner similar to that of compound 16 using ethylamine instead of methylamine, MS 405.35 (M+1).

EXAMPLE 9

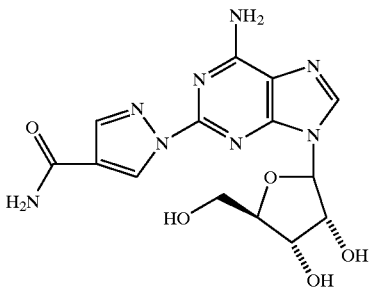

1-{9-[(4S,2R,3R,5R)-3,4-dihydroxy-5-(hydroxymethyl)oxolan-2-yl]-6-aminopurin-2-yl}pyrazole-4-carboxamide (20)

Compound 20 was prepared in a manner similar to that of compound 16 using ammonia instead of methylamine, MS 377.25 (M+1).

EXAMPLE 10

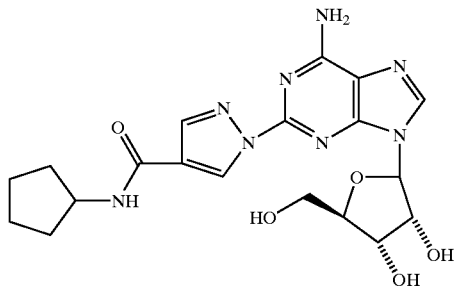

(1-{9-[(4S,2R,3R,5R)-3,4-dihydroxy-5-(hydroxymethyl)oxolan-2-yl]-6-aminopurin-2-yl}pyrazol-4-yl)-N-(cyclopentyl)carboxamide (21)

Compound 12 (0.5 g, 1.2 mmol) was dissolved in dry DMF, TBDMSCl (1.5 g, 10 mmol) and imidazole (0.68 g, 10 mmol) were added and the mixture was heated at 80° C. for 24 h. The solvent was evaporated and the residue was purified by flash column to obtain the trisilyl protected form of compound 12. The trisilyl derivative (0.8 g) was then suspended in 1 mL of water and treated with 2 m L1N KOH/MeOH. The mixture was stirred at RT for 72. The solvent was removed under reduced pressure and the residue was suspended in 5 mL of water and acidified to pH 5.5 with 1N HCl. The resulting precipitate was filtered and washed with water and ethyl ether to afford the trisilyl form of the acid 20.

The trisilyl derivative acid 20 (0.14 g, 0.2 mmol) was then dissolved in 5 mL dichloromethane. To the solution was added HBTU (0.19 g, 0.4 mmol), HOBt (0.076 g, 4 mmol), N-methylmorpholine (0.04 g, 0.4 mmol) and cat. DMAP. The mixture was allowed to stir at RT for 24 h. The mixture was then washed with 10% citric acid, saturated NaHCO$_3$, brine and dried over MgSO$_4$. The solvent was removed and the residue was treated with 5 mL 0.5N NH$_4$F/MeOH. The solution was heated at reflux for 24 h. The solvent was evaporated and the residue was purified by preparative TLC to afford compound 21, MS 445.26 (M+1).

EXAMPLE 11

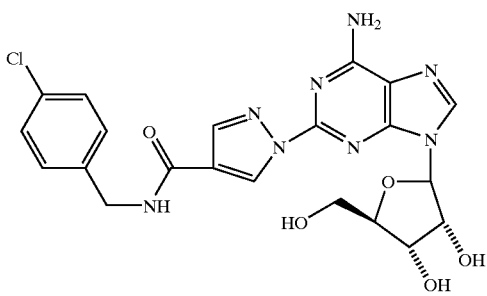

(1-{9-[(4S,2R,3R,5R)-3,4-dihydroxy-5-
(hydroxymethyl)oxolan-2-yl]-6-aminopurin-
2yl}pyrazol-4yl)-N-[(4-chlorophenyl)methyl]
carboxamide (22)

Compound 22 was prepared in a manner similar to that of compound 21 using 4 chlorobenzylamine instead of cyclopentylamine, MS 501.19 (M+1).

EXAMPLE 13

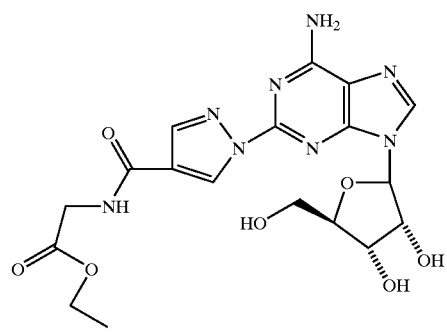

Ethyl 2-[(1-{9-(4S,2R,3R,5R)-3,4-dihydroxy-5-
(hydroxymetbyl)oxolan-2-yl]-6-aminopurin-2-
yl}pyrazol-4-yl)carbonylaminolacetate (23)

Compound 23 was prepared in a manner similar to that of compound 21 using glycine methyl ester instead of cyclopentylamine, MS 445.26 (M+1).

EXAMPLE 14

Compounds of this invention were assayed to determine their affinity for the $A_{2A}$ receptor in a pig striatum membrane prep. Briefly, 0.2 mg of pig striatal membranes were teated with adenosine deaminase (2 U/mL) and 50 mM Tris buffer (pH=7.4) followed by mixing. To the pig membranes was added 2 µL of serially diluted DMSO stock solution of the compounds of this invention at concentrations ranging from 10 nM to 100 microM or the control received 2 microL of DMSO alone, then the antagonist ZM 241385 in Tris buffer (50 mM, pH of 7.4) was added to achieve a final concentration of 2nM . After incubation at 23> C. for 2 h, then the solutions were filtered using a membrane harvester using multiple washing of the membranes (3x). The filter disks were counted in scintillation cocktail to determine the amount of displacement of tritiated ZM displaced by the compounds of this invention. Greater than a 5 point curve was used to generate Ki.'s and the number of experiments is indicated in the column marked in Table 1 below.

TABLE 1

| Compound Number | $A_{2a}$ Ki, nM | n |
| --- | --- | --- |
| 12 | +++ | 2 |
| 13 | ++ | 3 |
| 14 | ++ | 1 |
| 15 | ++ | 3 |
| 16 | ++ | 2 |
| 17 | − | 1 |
| 18 | +++ | 3 |
| 19 | +++ | 3 |
| 20 | +++ | 3 |
| 21 | +++ | 3 |
| 22 | +++ | 3 |

+++ = 10–1,000 nM
++ = 1,000–10,000 nM
+ = greater than 10,000 nM
− = greater than 100,000 nM

EXAMPLE 15

The objective of this experiment was to determine the affinities and receptor binding selectivity of a compound of this invention for $A_1$, $A_{2A}$, $A_{2B}$ and $A_3$ adenosine receptors. Molecular cloning has identified and confirmed the existence of four subtypes of adenosine receptors (AdoRs), designated as $A_1$, $A_{2A}$, $A_{2B}$ $_{and}$ $_{A3}$AdoRs (Linden, 1994). These AdoR subtypes have distinct anatomical distributions, pharmacological properties and physiological functions (Shryock and Belardinelli, 1997). $A_1$ and $A_3$AdoRs couple to inhibitory G proteins ($G_{i/o}$) and decrease the activity of adenylyl cyclase, whereas $A_{2A}$ and $A_{2B}$AdoRs increase intracellular cAMP content via coupling to stimulatory G proteins (Gs).

Ligands with high potency and tissue/organ selectivity for distinct adenosine receptor subtypes have therapeutic and diagnostic potentials for a variety of diseases (such as arrhythmia, ischemic heart diseases, asthma and Parlinson's disease) and are the focus of considerable research efforts by both academia and industry. Here we report the pharmacological and functional characterization of a series of novel adenosine analogues of this invention using mammalian cell lines expressing either endogenous AdoRs or recombinant human AdoRs.

Materials

Adenosine deaminase was purchased from Boehringer Mannheim Biochemicals Indianapolis, Id., U.S.A). [$^3$H] ZM241385 (Lot No. 1) was purchased from Tocris Cookson Ltd (Langford, Bristol, UK). [$^3$H]CPX (Lot No. 3329207) was from New England Nuclear (Boston, Mass., USA). CGS21680 (Lot No. SW-3R-84 and 89H4607), NECA (Lot No. OXV-295E), R-PIA (Lot No. WY-V-23), Rolipram and HEK-hA$_{2A}$R membranes were obtained from Sigma-RBI (Natick, Mass.). WRC-0470 was prepared as described in the literature (K. Nuiya et al., J. Med. Chem. 35; 4557–4561 (1992); Compound 16 of this invention was synthesized as described above and prepared as a stock solution (10 mmol/ L) in DMSO.

Cell culture and membrane preparation—PC12 cells were obtained from the American Type Culture Collection and grown in DMEM with 5% fetal bovine serum, 10% horse serum, 0.5 mmol/L L-glutamine, 100 U/mL penicillin, 0.1 mg/mL streptomycin, and 2.5 µg/mL amphotericin. HEK-293 cells stably expressing recombinant human $A_{2B}$AdoRs (HEK-hA$_{2B}$AdoR) were grown in DMEM supplemented with 10% fetal bovine serum and 0.5 mg/mL G-418. CHOK1 cells stably expressing the recombinant human $A_1$ AdoR (CHO-hA$_1$AdoR) and $A_3$AdoR (CHO-hA$_3$AdoR)

were grown as monolayers on 150-mm plastic culture dishes in Ham's F-12 media supplemented with 10% fetal bovine serum in the presence of 0.5 mg/mL G-418. Cells were cultured in an atmosphere of 5% $CO_2$/95% air maintained at 37° C.

To make membranes, cells were detached from the culture plates into ice-cold 50 mmol/L Tris-HCl buffer (pH7.4). The cell suspensions were homogenized with Polytron at setting 4 for 30 seconds, and spun at 48,000g for 15 minutes. The pellets were washed three times by re-suspension in ice-cold Tris-HCl buffer and centrifugation. The final pellet was re-suspended in a small volume of Tris-HCl, aliquoted and frozen at −80° C. until used for receptor binding assays. The protein concentration of membrane suspensions was determined using the Bradford method (Bio-Rad) with bovine serum as standards.

Competition Binding Assays—Competition assays were performed to determine the affinities ($K_i$) of the following unlabeled compounds (competing agents): Compounds WRC-0470; Compound 16 of this invention, NECA, CGS 21680 and R-PIA for $A_1$ AdoRs (R[$^3$H]DPCPX binding sites on CHO-hA$_1$AdoR cell membranes), $A_{2A}$ AdoRs(R[$^3$H]ZM241385 binding sites on PC12 and HEK-hA$_{2A}$AR cell membranes), $A_{2B}$AdoR (R[$^3$H]DPCPX binding sites on HEK-h$_{A2}$AdoR cell membranes) and $A_3$AdoR (R[$^{125}$I]ABMECA binding sites on CHO-hA$_3$AdoR cell membrane).

Membrane suspensions were incubated for 2 hours at room temperature in 50 mmol/L Tris-HCl buffer (pH 7.4) containing ADA (1 U/mL), Gpp(NH)p (100 μM), radioligand {either [$^3$H]ZM241385 (−1.5 to 5 mmol/L), [$^3$H]DPCPX (~2.5 to 3.0 mmol/L for $A_1$ and 30 nM for $A_{2B}$) or [$^{125}$I]ABMECA (1 nM)} and progressively higher concentrations of the competing agents. At the end of incubation, bound and free radioligands were separated by filtration through Whatman GF/C glass fiber filters using a Brandel tissue harvester (Gaithersburg, Md.). Triplicate determinations were performed for each concentration of the competing agent.

Study Design (Protocols)

The affinity (KY) of various CVT compounds for the $A_1$ and $A_{2A}$ adenosine receptor were determined by their potency to compete for [$^3$H]CPX ($A_1$) or [3H]ZM241385 ($A_{2A}$) binding sites on membranes derived from CHO-hA$_1$AdoR, PC12 or HEK-HA$_{2A}$AdoR cells. R-PIA and CGS21680, agonists that are selective for $A_1$ and $A_{2A}$ respectively, and NECA, a non-selective AdoR agonist were used as controls. To facilitate comparison and avoid the complication of multiple affinity states due to receptor coupling to G-proteins, the competition binding studies were carried out in the presence of Gpp (NH) p (100 μM) to uncouple receptors from G-proteins. The affinity of selected compounds for $A_{2A}$ and $A_3$ receptors were assessed by their potencies to compete for [$^3$H] CPX ($A_{2A}$) and [$^{125}$I] ABMECA (A3) binding sites on membranes derived from HEK-hA$_{2A}$AdoR and CHO-hA$_3$AdoR cells, respectively.

Results

The affinity ($K_i$) of WRC-0470; and Compound 16 for human $A_1$, rat and human $A_{2A}$AdoRs, as determined by competition binding studies are summarized in Table 2, below. All compounds show moderate selectivity for human $A_{2A}$ versus $A_1$ receptor. Furthermore, Compound 16, at a concentration of 10 μM, decreased the specific binding of [$^3$H] CPX (HEK-hA$_{2B}$AdoR) or [$^{125}$I] IBMECA (CHO-hA$_3$AdoR) by 20% and 22%, respectively.

TABLE 2

Binding Affinities of Adenosine Receptor Agonists for $A_{2A}$AdoRs and $A_1$AdoRs
$K_i$/nmol/L (p$K_i$ ± SEM)

|  | HEK-hA$_{2A}$AR Cells | | CHO-hA$_1$AR | |
|---|---|---|---|---|
|  | Binding Affinity | n | Binding Affinity | n |
| WRC-0470 | 272 | 6 | 7278 | 3 |
|  | (6.55 ± 0.04) |  | (5.16 ± 0.09) |  |
|  | [0.83 ± 0.07] |  | [1.13 ± 0.21] |  |
| Compound 16 | 1269 | 7 | >16460 | 3 |
|  | (5.90 ± 0.03) |  | (4.59 ± 0.35) |  |
|  | [0.73 ± 0.04] |  | [0.92 ± 0.04] |  |
| CGS21680 | 609 | 3 | >3540 | 3 |
|  | (6.22 ± 0.06) |  | (5.47 ± 0.20) |  |
|  | {0.65 ± 0.07} |  |  |  |
| NECA | 360 | 3 | 328 | 3 |
|  | (6.45 ± 0.06) |  | (6.49 ± 0.06) |  |
|  | [0.83 ± 0.08] |  | [0.88 ± 0.03] |  |
| R-PIA | 1656 | 3 | 477 | 3 |
|  | (5.78 ± 0.02) |  | (6.35 ± 0.11) |  |
|  | [1.05 ± 0.02) |  | [1.03 ± 0.08] |  |

The results of this Experiment show that Compound 16 is a low affinity $A_{2A}$ agonist.

EXAMPLE 16

The objective of this Example was to characterize pharmacologically the effects of Compound 16 of this invention on coronary artery conductance. Specifically, the experiments were designed to determine 1) the potency Compound 16 and compared its potency to that of adenosine and other selected $A_{2A}$ doR agonists, and 2) which adenosine receptor, the $A_1$ or $A_{2A}$ AdoR subtype mediates the coronary vasodilation caused by Compound 16 of this invention.

In the heart, the $A_{2A}$ adenosine receptor mediates the coronary vasodilation caused by adenosine, whereas the $A_i$ receptor mediates the cardiac depressant actions of adenosine, such as the negative chronotropic and dromotropic (AV block) effects.

Several potent and selective ligands, both agonists and antagonists, for the $A_1$ and $A_{2A}$ AdoRs have been synthesized. In the heart agonists of $A_1$ AdoRs have been proposed to be useful as antiarrhythmic agents, whereas agonists of $A_{2A}$ AdoRs are being developed for selective coronary vasodilation A series of adenosine derivatives targeted for selective activation of $A_{2A}$, adenosine receptor ($A_{2A}$doR) were synthesized for the purposes of developing coronary vasodilators. More specifically, in this study we report on the effect of a series of novel $A_{2A}$ AdoR agonists on coronary artery conductance (vasodilation) in rat and guinea pig isolated perfused hearts.

Materials

Rats (Sprague Dawley) and Guinea pigs (Hartley) were purchased from Simonsen and Charles Rivers, respectively. WRC-0470 was prepared as described in the literature (K. Niiya et al., J. Med. Chem. 35; 4557–4561 (1992). Compound 16 of this invention was prepared as described above. CGS 21680 and adenosine were purchased from Sigma Krebs-Henseleit solution was prepared according to Standard Methods, and 0.9% saline was purchased from McGraw, Inc.

Methods

Adult Sprague Dawley rats and Hartley guinea-pigs of either sex weighing from 230 to 260 grams and 300 to 350 grams, respectively were used in this study. Animals were anesthetized by peritoneal injection of a cocktail containing ketamine and xylazine (ketamine 100 mg, xylazine 20 mg/ml). The chest was opened and the heart quickly removed. The heart was briefly rinse in ice-cold Krebs-Henseleit solution (see below), and the aorta cannulated. The heart was then perfused at a flow rate of 10 ml/min with modified Krebs-Henseleit (K-H) solution containing NaCl 117.9, KCl 4.5, $CaCl_2$ 2.5, $MgSO_4$ 1.18, $KH_2PO_4$ 1–18, pyruvate 2.0 mmo/L. The K-H solution (pH 7.4) was gassed continuously with 95% 0.2 and 5% $CO_2$ and warmed to ±0.50° C. The heart was electrically paced at a fixed cycle length of 340 ms (250 beats/min) using a bipolar electrode place on the left atrium. The electrical stimuli were generated by a Grass stimulator (Model S48, W. Warwick, R.I.) and delivered through a Stimuli Isolation Unit (Model SIUS, Astro-Med, Inc., N.Y.) as square-wave pulses of 3-msec in duration and amplitude of at least twice the threshold intensity.

Coronary perfusion pressure (CPP) was measured using a pressure transducer, connected to the aortic cannula via a T-connector positioned approximately 3 cm above the heart Coronary perfusion pressure was monitored throughout the experiment and recorded either on a chart recorder (Gould Recorder $^{2200}$S) or a computerized recording system (PowerLab/4S, ADinstruments Pty Ltd, Australia). Only hearts with CPP ranging from 60 to 85 mmHg (in the absence of drugs) were used in the study. Coronary conductance (in ml/min/mmHg) was calculated as the ratio between coronary perfusion rate (10 ml/min) and coronary perfusion pressure.

In experiments in which $A_1$ adenosine receptor-mediated negative dromotropic effect was measured, atrial and ventricular surface electrograms were recorded during constant atrial pacing. The effect of various adenosine receptor agonists on atrioventricular conduction time was determined as described previously by Jenkins and Belardinelli *Circ. Res.* 63:97–116 (1988).

Stock solutions of Compound 16 of this invention (5mM) and CGS 21680 (5mM) were prepared in dimethyl sulfoxide (DMSO); purchased from Aldrich, PS 04253MS. A stock solution of adenosine (1 mg/ml) was prepared in saline. One concentration was made from the stock solution by dilution into saline to yield solution of either $2 \times 10^4$ or $2 \times 10^{-5}$ M. These solutions were injected into the perfusion line of the apparatus as boluses of 20 μL. In some experiments the solutions were placed into a 30 ml glass syringe and the drugs were infused at rates necessary to achieve the desired perfusate concentrations (e.g, 10, 100 nM, etc).

Coronary Vasodilation of $A_2$ Adenosine Receptor Agonists

Concentration-response relationships for the effect of Compound 16 of this invention (0.1 to 400 nmM) and CGS21680 (0.1 to 10 nM) to increase coronary conductance were obtained. After control measurements of coronary perfusion pressure were recorded, progressive higher concentrations of the adenosine receptor agonists were administered until maximal coronary vasodilation was observed. The steady-state responses to each concentration of adenosine receptor agonists were recorded. In each heart of this series (4 to 6 hearts for each agonist) only one agonist and one concentration-response relationship was obtained
Coronary Vasodilatory Effect of Compound 16 in the Absence and Presence of Adenosine Receptor Antagonists.

To determine which adenosine receptor subtype ($A_1$ or $A_{2A}$) mediates the coronary vasodilation caused by Compound 12, the $A_1$ and $A_{2A}$, adenosine receptor antagonists CPX and ZM241385, respectively, were used. Hearts (n=6) were exposed to the compound being tested (10 nM), and after the effect of this agonist reached steady-state, first CPX (60 nM), and then ZM241385 were added to the perfusate and the changes in CPP were recorded.

In isolated perfused hearts (n=36 rats and 18 guinea pigs) paced at constant atrial cycle length of 340 msec, adenosine, CGS21680, WRC0470, and Compound 16 caused a concentration-dependent increase in coronary conductance. CGS21680 and WRC0470 were the most potent agonists tested. Compound 16 was approximately 10-fold more potent than adenosine to increase coronary conductance. It is worth noting that all agonists were several fold more potent coronary vasodilators in rat than guinea pig hearts (Table 3).

TABLE 3

Potency of Adenosine and $A_{2A}$ Adenosine Receptor Agonists to Increase Coronary Conductance in Rat and Guinea Pig Isolated Perfused Hearts

| | | Potency ($EC_{50}$) | |
|---|---|---|---|
| Agonist | n | Rat | Guinea Pig |
| Compound 16 | 4 | 6.4 ± 1.2 | 18.6 ± 6.0 |
| Adenosine | 4 | 59.2 ± 6.4 | 86.0 ± 0.5 |
| CGS21680 | 4 | 0.5 ± 0.1 | 1.7 ± 0.4 |
| WRC0470 | 3 | 0.6 ± 0.2 | 2.4 ± 1.1 |

Figure 1B:
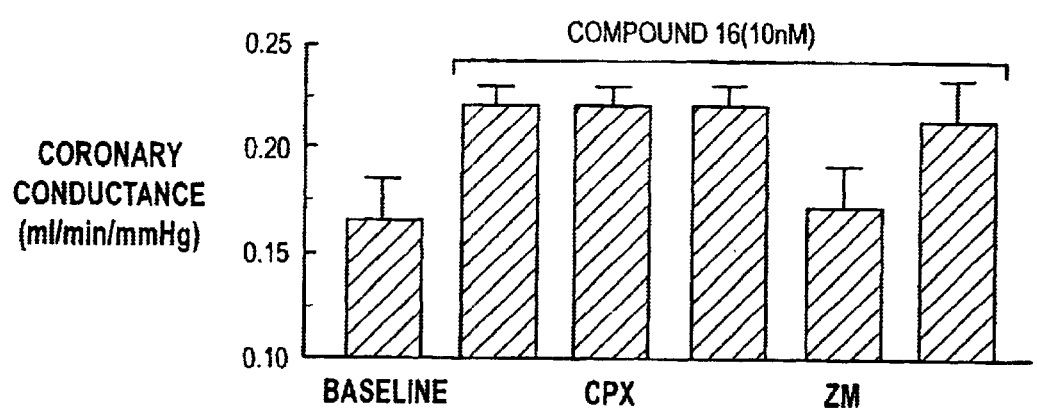
FIG. 1B is a summary of the data shown in FIG. 1A showing that CPX did not but that ZM241385 did attenuate the increase in coronary conductance caused by Compound 16 of this invention.

To determine the AdoR subtype ($A_1$ versus $A_{2A}$) that is responsible for the coronary vasodilation observed in the presence of Compound 16, the effect of this agonist (10 nM) on coronary conductance was studied in the absence and presence of CPX, a selective $A_{2A}$ AdoR antagonist (Belardinelli et al, 1998) and ZM241385, a selective $_{A2}$ AdoR antagonist (Poucher et al, 1 995) at the concentration of 60 nM. As shown in FIG. 1, Compound 16 significantly increased coronary conductance to 0.22+0.01 ml/mm $Hg^{-1}$ $min^-$ from a baseline value of 0.16+0.02 $mlmmHg^{-1}$ $min^{-1}$. This increase in coronary conductance caused by Compound 16 was not affected by CPX but was completely reversed by ZM241385 (0.17±0.02 mlmm Hg-1 $min^{-1}$).

EXAMPLE 17

The objective of this Example was to determine the functional selectivity of Compound 16 to cause coronary vasodilation. Specifically, the potency of Compound 16 to cause coronary vasodilation ($A_{2A}$ AdoR response) and prolongation of A-V nodal conduction time ($A_1$ AdoR response) were determined in rat and guinea pig hearts.
Materals Sprague Dawley rats were purchased from Sirnonsen. Hartley guinea pigs were purchased from Charles River. Compound 16 was prepared as described above. CVT-510-2-{6[((3R)oxolan-3-yl)amino]purin-9-yl}(4S,3R,5R)-(hydroxymethyl)oxolane-3,4-diol—was prepared in accordance with the synthesis method disclosed in U.S. Pat. No. 5,789,416, the specification of which is incorporated herein by reference. Ketamine was purchased from Fort Dodge Animal Health (Lot No. 440444) and xylazine from Bayer (Lot No. 26051 A). Krebs-Henseleit solution was prepared according to the standard methods, and 0.9% sodium chloride was purchased from McGraw, Inc. (Lot No. J8B246).
Isolated Perfused Heart Preparation:

Rats and guinea pigs, of either sex weighing from 230 to 260 grams and 300 to 350 grams, respectively, were used in this study. Animals were anesthetized by peritoneal injection of a cocktail containing ketamine and xylazine (ketamine 100 mg, xylazine 20 mg/ml). The chest was opened and the heart quickly removed. The heart was briefly rinse in ice-cold Krebs-Henseleit solution (see below), and the aorta cannulated. The heart was then perfused at a flow rate of 10 ml/min with modified Krebs-Henseleit (K-H) solution containing NaCl 117.9, KCl 4.5, $CaC_22.5$, $MgSO_41.18$, $KH_2PO_41.18$, pyruvate 2.0 mmo/L. The K-H solution (pH 7.4) was gassed continuously with 95% [2] and 5% $CO_2$ and warmed to 35±0.50° C. The heart was electrically paced at a fixed cycle length of 340 ms (250 beats/min) using a bipolar electrode place on the left atrium. The electrical stimuli were generated by a Grass stimulator (Model S48, W. Warwick, R.I.) and delivered through a Stimuli Isolation Unit (Model SIU5, Astro-Med, Inc., N.Y.) as square-wave pulses of 3-msec in duration and amplitude of at least twice the threshold intensity.

Coronary perfusion pressure (CPP) was measured using a pressure transducer, connected to the aortic cannula via a T-connector positioned approximately 3 cm above the heart. Coronary perfusion pressure was monitored throughout the experiment and recorded either on a chart recorder (Gould Recorder 2200S) or a computerized recording system (PowerLab/4S, ADinstunents Pty Ltd, Australia). Only hearts with CPP ranging from 60 to 85 mmHg (in the absence of drugs) were used in the study. Coronary conductance (in ml/min/mmHg) was calculated as the ratio between coronary perfusion rate (10 ml/min) and coronary perfusion pressure.

$A_1$ adenosine receptor-mediated depression of A-V nodal conduction time (negative dromotropic effect) was measured. Atrial and ventricular surface electrograms in rats and His bundle electrogram in guinea pigs, were recorded during constant atrial pacing. The effects of Compound 16 on atrioventricular conduction time and stimulus-to-His-bundle (S-H interval) were determined as described previously by Jenkins and Belardinelli (1988).

The effects of Compound 16 on coronary conductance ($A_{2A}$ effect) and atrioventricular conduction time or stimulus-to-His-bundle. (S-H) interval ($A_1$ ueffect) was then determined. Hearts were instrumented for continuous recording of coronary perfusion pressure ($A_2A$ response) and atrioventricular (A-V) conduction time or S-H interval ($A_1$ response). In each experiment, concentration-response relationship of Compound 16 (n=6 rats, 4 guinea pigs) to increase coronary conductance and to prolong A-V conduction time or S-H interval was determined. After control measurements of CPP and A-V conduction time or S-H interval were made, progressive higher concentrations of Compound 16 was administered until maximal coronary vasodilation and A-V nodal conduction time or S-H interval prolongation were achieved. In separate rat hearts (n=4), the effect of various concentrations (100–400 nM) of CVT510, an $A_1$ adenosine agonist (Snowdy et al, 1999), on A-V nodal conduction time was determined and compared to that of Compound 16 (0.1–30 µM).

Figure 2:
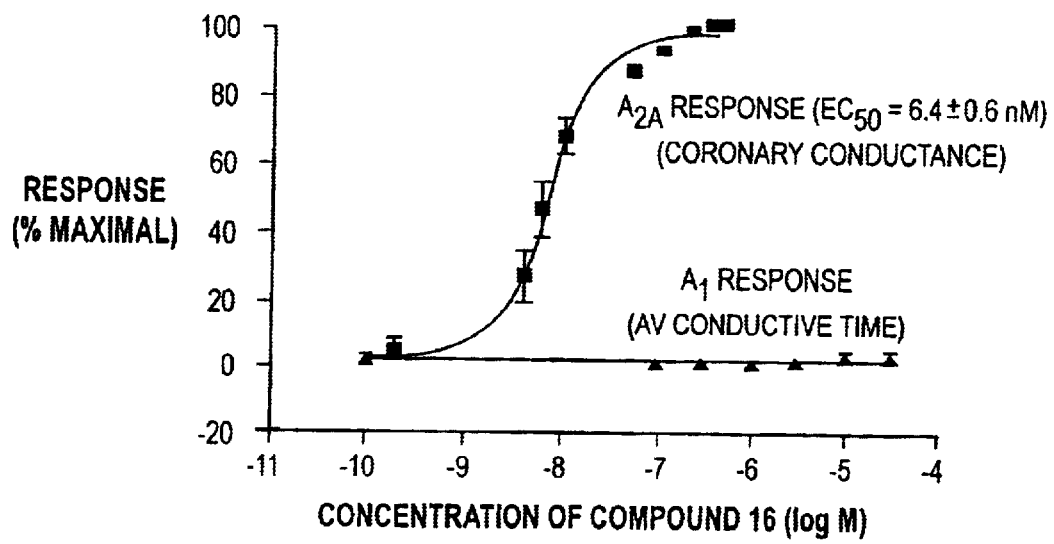
FIG. 2 is a concentration response curve for the $A_1$ adenosine receptor (AdoR)-mediated negative dromotropic (AV conduction time) and $A_{2A}$ AdoR-mediated vasodialator (increase coronary conductance) effects of Compound 16 in rat isolated perfused hearts. Symbols and error bars indicate means±SEM of single determination from each of four hearts. $EC_{50}$ value (potency) is the concentration of Compound 16 that causes 50% of maximal response.
Figure 3:
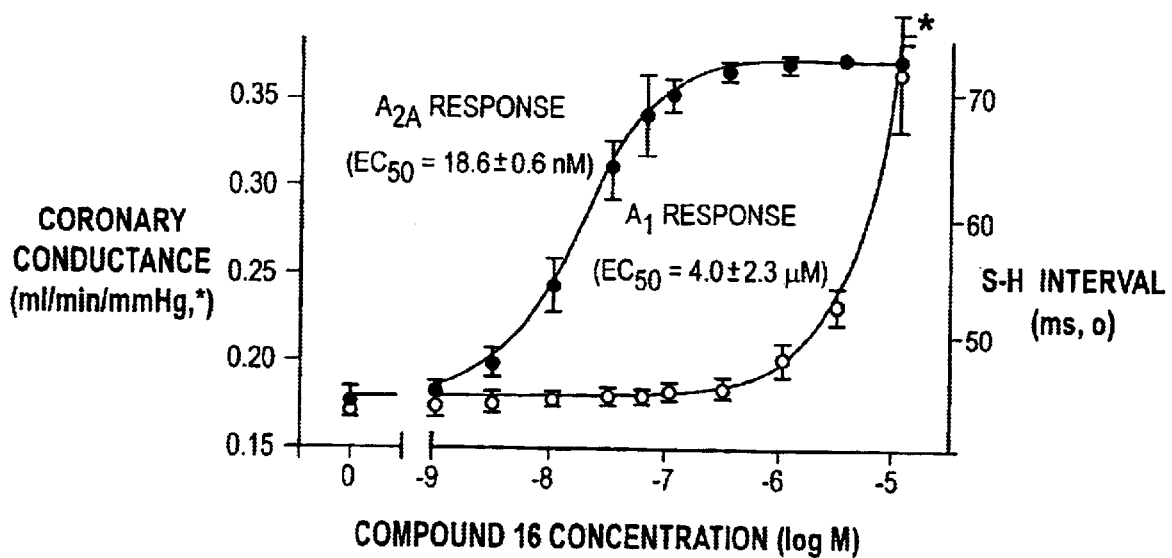
FIG. 3 is a concentration response curve for the Al adenosine receptor (AdoR)-mediated negative dromotropic (AV conduction time) and $A_{2A}$ AdoR-mediated vasodialator (increase coronary conductance) effects of Compound 16 in guinea pig isolated perfused hearts. Symbols and error bars indicate means±SEM of single determination from each of four hearts. $EC_{50}$ value (potency) is the concentration of Compound 16 that causes 50% of maximal response.
Figure 4:
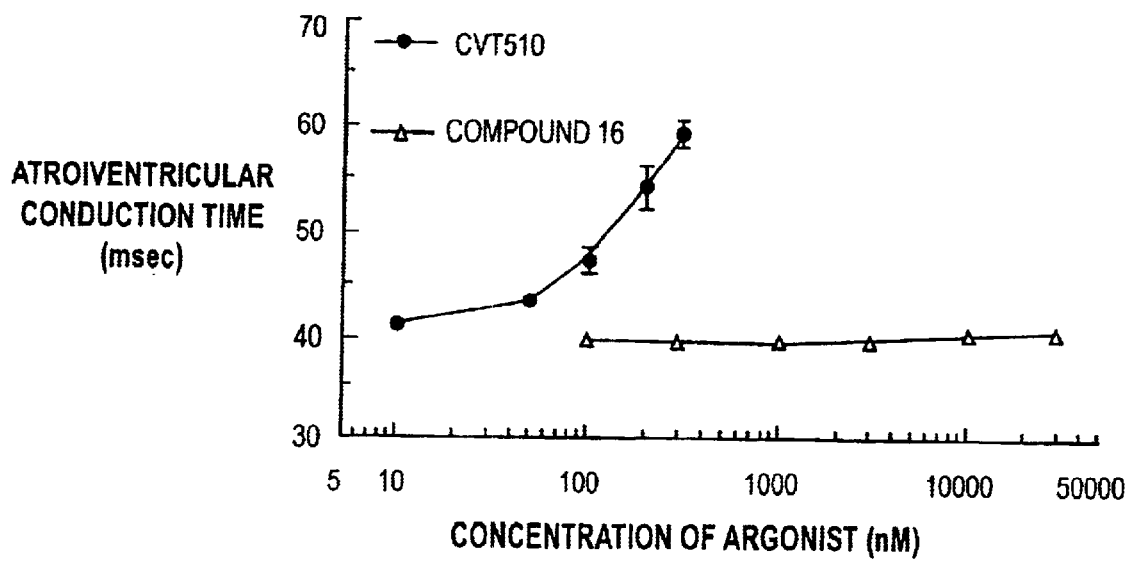
FIG. 4 is a plot of the effect of CVT510, an $A_1$ adenosine receptor agonist and Compound 16 of this invention, an $A_{2A}$ adenosine receptor agonist on atrioventricular (AV) conduction time in rat isolated perfused hearts.

The concentration-response curves for Compound 16 to increase coronary artery conductance and to prolong A-V nodal conduction time or S-H internal are shown in FIGS. 2 and 3. In both rat and guinea pig, Compound 16 increased coronary conductance in a concentration dependent manner. The potencies ($EC_{50}$ values) for Compound 16 to increase coronary conductance in rat hearts was 6.4±0.6 nM and in guinea pig hearts was 18.6±6 OnM. In contrast, the effect of this agonist on S-H interval was somewhat variable between rat and guinea pig hearts. In rat hearts Compound 16 did not prolong A-V nodal conduction time (FIGS. 2 and 3) whereas the $A_1$ AdoR agonist CVT510 significantly prolonged the A-V nodal conduction time (FIG. 4). Unlike in rat, in guinea pig hearts Compound 16 caused a concentration-dependent prolongation of S-H interval (A1 response) with an $EC_{50}$ value (potency) of 4.0±2.3 µM (FIG. 4). This latter value is approximately 215-fold greater (i.e., less potent) than the $EC_{50}$ value of 18.6±6.0 nM to cause coronary vasodilation ($A_{2A}$ response-FIG. 3).

The results indicate that Compound 16 is a coronary vasodilator ($A_{2A}$ AcdoR-mediated effect) devoid of negative dromotropic effect ($A_1$ AdoR-mediated effect) in rat hearts. In guinea pig hearts Compound 16 caused some negative dromotropic effect. Nevertheless, Compound 16 was at least 215-fold more selective to cause coronary vasodilation than negative dromotropic effect. The reason(s) for the species difference in the $A_1$ AdoR-mediated response elicited by Compound 16 is unknown. Regardless, in both species (rat and guinea pig) Compound 16 causes maximal coronary vasodilation at concentrations that do not cause prolongation of A-V nodal conduction time, i.e., without negative dromotropic effect. It was also observed that Compound 16 has a greater affinity (i.e., >2-/>-13-fold) for $A_{2A}$ than $A_1$ AdoR and that there is a markedly greater receptor reserve for $A_{2A}$ AdoR-mediated coronary vasodilation than for $A_1$ AdoR-mediated negative dromotropic effect.

EXAMPLE 18

The present study was designed to test the hypothesis that there is an inverse relationship between the affinity ($K_i$ or $pK_i$) and duration of action of $A_2$ adenosine receptors (AdoR). Specifically, the aims of the study were to determine the relationship between the duration of the coronary vasodilation caused by a selected series of high and low affinity $A_{2A}$ AdoR agonists in rat isolated hearts and anesthetized pigs; and the affinity of these agonists for $A_{2A}$ doRs in pig striatum.

Materials: Rats (Sprague Dawley) were purchased from Simonen. Farm pigs were obtained from Division of Laboratory Animal Resources, University of Kentucky. Compound 12, Compound 13, and Compound 16 of this invention were prepared as described in the methods above. YT-0146 was prepared as described in U.S. Pat. No. 4,956, 345, the specification of which is incorporated herein by reference. WRC-0470 was prepared as described in the literature (K. Niiya et al., J. Med. Chem. 35; 4557–4561 (1992). CGS21680 was purchased from Research Biochemicals, Inc. and Sigma and R-PIA (Lot No. WY-V-23) was purchased from Research Biochemicals, Inc. HENECA was a gift from Professor Gloria Cristalli of University of Camerino, Italy.

The anesthetic agents: Ketamine was purchased from Fort Dodge Animal Health. Xylazine was purchased from Bayer. Sodium pentobarbital was purchased from The Butler Co. Phenylephrine was purchased from Sigma DMSO was purchased from Sigma and American Tissue Type Collections. Krebs-Henseleit solution was prepared according to standard methods, and 0.9% saline was purchased from McGraw, Inc.

In this study, the following laboratory preparations were used. 1) Rat isolated perfused hearts; 2) Anesthetized open-chest pigs;

Rat Isolated Perfused Heart Preparation

Adult Sprague Dawley rats of either sex weighing from 230 to 260 grams were used in this study. Animals were anesthetized by peritoneal injection of a cocktail containing ketamine and xylazine (ketamine 100 mg, xylazine 20 mg/ml). The chest was opened and the heart quickly removed. The heart was briefly rinse in ice-cold Krebs- Henseleit solution (see below), and the aorta cannulated. The heart was then perfused at a flow rate of 10 ml/min with modified Krebs-Henseleit (K-H) solution containing NaCl 117.9, KCl 4.5, CaCl. 2.5, $MgSO_4$1.18, KH2PO4 1.18, pyruvate 2.0 mmo/L. The K-H solution (pH 7.4) was gassed continuously with 95% $_2$ and 5% $CO_2$ and warmed to 35±0.50° C. The heart was electrically paced at a fixed cycle length of 340 ms (250 beats/min) using a bipolar electrode-place on the left atrium. The electrical stimuli were generated by a Grass stimulator (Model S48, W. Warwick, R.I.) and delivered through a Stimuli Isolation Unit (Model SIU5, Astro-Med, Inc., N.Y.) as square-wave pulses of 3 msec in duration and amplitude of at least twice the threshold intensity.

Coronary perfusion pressure (CPP) was measured using a pressure transducer, connected to the aortic cannula via a T-connector positioned approximately 3 cm above the heart Coronary perfusion pressure was monitored throughout the experiment and recorded either on a chart recorder (Gould Recorder $^{2200}$S) or a computerized recording system (PowerLab/4S, ADInstruments Pty Ltd, Australia). Only hearts with CPP ranging from 60 to 85 mmHg (in the absence of drugs) were used in the study. Coronary conductance (in ml/min/mmHg) was calculated as the ratio between coronary perfusion rate (10 ml/min) and coronary perfusion pressure.

Anesthetized Open-chest Pig Preparation

Farm pigs weighing 22–27 kg were used in this study. All animals received humane care according to the guidelines set forth in The Principles of Laboratory Animal Care formulated by the National Society for Medical research and the "Guide for the Care and Use of Laboratory Animals" prepared by the Institute of Laboratory Animal Resources and published by the National Institutes of Health (NIH Publication No. 86–23, revised 1996). In addition, animals were used in accordance with the guidelines of the University of Kentucky Institutional Animal Care and Use Protocol.

Anesthesia was anesthetized with ketamine (20 mg/kg, i.m.) and sodium pentobarbital (15–18 mg/kg i.v.). Anesthesia was maintained with additional sodium pentobarbital (1.5–2 mg/kg, i.v.) every 15–20 minutes. Ventilation was maintained via a tracheotomy using a mixture of room air and 100% 02. Tidal volume, respiratory rate and fraction of $_2$ in inspired air were adjusted to maintain normal arterial blood gas (ABG) and pH values. Core body temperature was monitored with an esophageal temperature probe and maintained with a heating pad between 37.0–37.5° C. Lactate Ringers solution was administered via an ear or femoral vein, at 5–7 ml/kg/min after a initial bolus of 300–400 ml. A catheter was inserted into the femoral artery to monitor arterial blood pressure and to obtain ABG samples.

The heart was exposed through a median sternotomy, and suspended in a pericardial cradle. Left ventricular pressure (LVP) was measured with a 5F high fidelity pressure sensitive tip transducer (Millar Instrunents, Houston, Tex.) placed in the left ventricular cavity via the apex and secured with a purse string suture. A segment of the left anterior descending coronary artery (LAD), proximal to the origin of the first diagonal branch, was dissected free of, surrounding tissue. A transit time perivascular flow probe (Transonic Systems Inc., Ithaca, N.Y.) was placed around this segment to measure coronary blood flow (CBF). Proximal to the flow probe a 24 g modified angiocatheter was inserted for intracoronary infusions. All hemodynic data were continuously displayed on a computer monitor and fed through a 32 bit analogdigital converter into an on line data acquisition computer with customized software (Augury, Coyote Bay Instruments, Manchester, N.H.). $A_{2A}$ AdoR agonists were dissolved in DMSO to produce stock concentrations of 1–5 mM, which were diluted in 0.9% saline and infused at rates of 1–1.5 ml/min. The $A_{2A}$ AdoR agonists were administered intracoronary. To maintain blood pressure constant, phenylephrine was administered intravenously. The phenylephrine stock solution (30 mM) was prepared in distilled water.

Isolated Perfused Hearts

To determine the duration of the $A_{2A}$ adenosine receptor mediated coronary vasodilation caused by adenosine and adenosine receptor agonists, the agonists were administered interveneously either by bolus injection (protocol A) or by continuous infusion (protocol B).

Protocol A: Bolus injections. In each heart of this series (3 to 11 hearts for each agonist), boluses of adenosine (20 μl, $2\times10^{-4}$ M), Compounds of this invention (20 to 40 μl, $2\times10^{-5}$ M), and other adenosine receptor agonists were injected into the perfusion line. The times to 50% (t 0.5) and 90%/o (t 0.9) reversal of the decrease in CPP were measured. Each heart was exposed to a maximum of three vasodilators.

Protocol B: Continuous infusion. In a separate series of experiments (n=4), Compound 16 and adenosine were infused into the perfusion line at constant rate for a period of six minutes. The perfusate concentrations of Compound 16 and adenosine were 20 nM and 200 nM respectively, which were approximately 4× their respective concentrations previously established to cause 50% of maximal increase in coronary conductance ($EC_{50}$) in rat isolated perfused hearts. The times to 50% (t 0.5) and 90% (t 0.9) reversal of the decreases in CPP were measured from the time at which the infusion of the agonists was stopped.

Dose-dependent duration of maximal vasodilation caused by bolus injections of Compound 16. To determine the dependency of the duration of maximal coronary vasodilation on the dose of Compound 16, boluses (100–300 μl) of a $2\times10^{-5}$ M stock solution of Compound 16 were injected into the perfusion line. In addition, the duration of the injection was varied according to the volume of the boluses such as 10, 20 and 30 sec for 100, 200 and 300 μl boluses respectively. The duration of maximal effect was measured from the point at which the decrease in CPP reached the nadir to the onset point of reversal of CPP.

Relationship between affinity of various agonists for $A_{2A}$ adenosine receptor and the reversal time of their effect to increase coronary conductance: These experiments were performed to construct the relationship between the affinities of the various agonists for $A_{2A}$ adenosine receptor and the duration of their respective effect on coronary conductance. Boluses of various agonists were injected into the perfusion line of rat isolated perfused hearts (n=4 to 6 for each agonist) and the time to 90% (t0.9) reversal of the decrease in CPP measured. The affinities of the various agonists for $A_{2A}$ adenosine receptor was determined in pig striatum membranes using a radioligand binding assay, as described above. The reversal time (t0.9) of the decrease in CPP was plotted against their affinities ($pK_i$) for the $A_{2A}$ adenosine receptor.

Open-chest Pig

Prior to initiating the experiment, a 30-minute stabilization period followed the completion of all instrumentation. After obtaining the baseline hemodynamic data the first intracoronary infusion of an $A_{2A}$ ADOR agonist was initiated Infusions were maintained for 4–5 minutes to allow LAD CBF to reach a steady state, after which the infusion was terminated. The time to recovery of 50% (t 0.5) and 90% (t0.9) of baseline CBF were recorded. Ten to 15 minutes after CBF returned to pre-drug values a second infusion with a different agonist was started. In preliminary studies it was found that the intracoronary infusion of adenosine agonists produced varying degrees of systemic hypotension, and hence, in all subsequent experiments, phenylephrine was administered intravenously. Hemodynamic measurements were made prior to and following the initiation of the phenylephrine infusion at dose of $-1$ μg/kg/min. The phenylephrine infision rate was adjusted during and following the infusions of the adenosine agonists to maintain arterial blood pressure within 5 mmHg of preinfusion values. The effect of a maximum of three different agonists was determined in each experiment.

Results

Adenosine, the compounds of this invention and other adenosine derivatives were given as boluses into the perfusion line at concentrations that cause equal or near-equal increases in coronary conductance. Although adenosine and the agonists caused equal maximal increases in coronary conductance the duration of their effect was markedly different. The duration of the effect of adenosine was the shortest followed by Compound 16, whereas that of CGS21680 and WRC6470 were the longest. The durations of the coronary vasodilation caused by adenosine, the compounds of this invention and other agonists measured as the time to 50% and 90% (t 0.5 and t 0.9, respectively) reversal of the increases in coronary conductance are summarized in Table 4

TABLE 4

Reversal Time Of Coronary Vasodilation by Adenosine and adenosine receptor agonists in Rat Isolated Perfused Hearts

| Agonist | t 0.5 (min) | t 0.9 (min) | n |
|---|---|---|---|
| Adenosine | 1.06 ± 0.1 | 5.6 ± 0.8 | 11 |
| HENECA | 28.6 ± 1.1 | 32.8 ± 2.1 | 3 |
| R-PIA | 7.9 ± 0.1 | 12.6 ± 0.8 | 3 |
| CGS21680 | 14.5 ± 0.9 | 19.5 ± 0.9 | 3 |
| YT-146 | 17.7 ± 1.0 | 28.5 ± 4.0 | 3 |
| Compound 12 | 14.83 ± 2.1 | 15.0 ± 0.8 | 3 |
| Compound 13 | 14.4 ± 1.9 | 21.3 ± 3.9 | 4 |
| Compound 16 | 5.2 ± 0.2 | 11.3 ± 1.1 | 5 |

Time (in minutes) to 50% and 90% (t 0.5 and t 0.9, respectively) reversal of the increases in coronary conductance caused by adenosine and adenosine receptor agonists. Values are the means ± SEM of single determinations in each of the preparations (n).

The reversal time of coronary vasodilation was dependent on the affinity of the adenosine derivatives for brain striatum $A_{2A}$ receptors. (FIG. 2A) There was a significant (P<0.05) inverse relationship (r=0.87) between the affinity (PKi) of the agonists for the $A_{2A}$ AdoR and the reversal time (t 0.9) of the coronary vasodilation caused by the same agonists.

Regardless of whether Compound 16 was given as bolus or continuous infuision the reversal of the coronary vasodilation was relatively rapid. In fact, a comparison between a six minute infusion of adenosine and Compound 16 at doses that they cause equal decreases in coronary perfusion pressure (CPP) revealed that adenosine and Compound 16 have a similar time course for vasodilation and reversal time. Both the t 0.5 and t 0.9 were near identical. The duration of the coronary vasodilation by Compound 16 was dose-dependent. Increasing the volume of a bolus of Compound 16 (stock solution of $2\times10^{-5}$ M) caused progressively longer lasting decreases in CPP. The maximal duration of the coronary vasodilation (time that CPP remained at its lowest) increased as the volume of the boluses increased from 100 μl to 200 and 300 μl without affecting the maximal decreases in CPP.

Coronary Vasodilation in an Open-chest Pig Preparation

In in situ hearts of an open-chest anesthetized pig preparation Compound 16 of this invention as well as CGS21680 and other $A_{2A}$AdoR agonists (i.e., WRC-0470 and YT-146) caused significant increases in coronary blood flow (CBF). Selected doses of these compounds given as continuous (4 to 5 min) intracoronary infusions caused 3.1 to 3.8-fold increases in CBF as set forth in Table 3, below. Once established that all agonists caused near the same magnitude of increases in CBF (i.e., "fold increase") and cause similar changes in heart rate and mean arterial blood pressure, the reversal time of their respective coronary vasodilation effects was determined.

TABLE 5

Magnitude of Increase in Coronary Blood Flow Caused by Various Adenosine Receptor Agonists in Open-Chest Anesthetized Pigs

| Agonist | CBF ("Fold Increase" | n |
|---|---|---|
| Compound 16 (10 μg/kg/min) | 3.40 ± 0.04 | 3 |
| Compound 16 (310 μg/kg/min) | 3.83 ± 0.39 | 6 |
| WRC-470 (1 μg/kg/min) | 3.14 ± 0.24 | 6 |
| GSC21680 (2 μg/kg/min) | 3.54 ± 0.093 | 3 |
| YT-146 (1 μg/kg/min) | 3.44 ± 0.47 | 3 |

Maximal "fold-increase" in coronary blood flow (CBF) above baseline caused by various adenosine receptor agonists. Data represent mean ± SEM of one or two measurements in each pig (n).

As summarized in Table 6 the $t_{0.5-}$ and $t_{0.9}$ of coronary vasodilation caused by the various $A_{2A}$ AdoR agonists and "CVT-compounds" was variable. The reversal time of the increase in CBF caused by Compound 16 of this invention were shorter than that of CGS21680, WRC-0470 or YT-146. More importantly, as in rat isolated perfused hearts, there was a significant (P<0.05) inverse relationship (r=0.93) between the affinity (PKi) of the $A_{2A}$ AdoR agonists for pig brain striatum $A_{2A}$ receptors and the reversal time (t 0.9) of coronary vasodilation. There was an excellent concordance between the reversal time of the coronary vasodilation caused by a selected number of agonists in rat isolated perfused hearts and in anesthetized open chest pig preparations.

TABLE 6

Reversal Time of Coronary Vasodilation Caused by Various Adenosine Receptor Agonists in Open-Chest Anesthetized Pigs

| Agonist | | $t_{0.5}$ (min) | $t_{0.9}$ (min) | n |
|---|---|---|---|---|
| Compound 16 | (10 μg/kg/min) | 1.9 ± 0.2 | 10.1 ± 0.7 | 3 |
| Compound 16 | (310 μg/kg/min) | 2.6 ± 0.4 | 12.3 ± 1.1 | 6 |
| WRC-470 | (1 μg/kg/min) | 9.5 ± 0.8 | 22.5 ± 1.6 | 6 |
| GS21680 | (2 μg/kg/min) | 9.7 ± 0.8 | 21.4 ± 0.8 | 3 |
| YT-146 | (1 μg/kg/min) | 17.8 ± 3.4 | 32.9 ± 5.6 | 3 |

Time (in minutes) to 50% and 90% (t $_{0.5}$ and t $_{0.9}$ respectively) reversal of the increases in coronary blood flow caused by adenosine receptor agonists. Values are the means ± SEM of one or two determinations in each animal (n).

Compound 16 is a low affinity $A_{2A}$ AdoR agonists and less potent ($-10$-fold) than the prototypical agonist CGS21680. Nevertheless Compound 16 is a full agonist to cause coronary vasodilation. But, as shown in this study the duration of its effect is several-fold shorter than that of the high affinity agonists CGS21680 and WRC-0470. Hence, Compound 16 is a short acting $A_{2A}$ AdoR agonists coronary vasodilator. Because of its short duration of action in comparison to the high affinity $A_{2A}$ AdoR agonists (e.g., WRC-0470, CGS21680) this low affinity but still full agonist coronary vasodilator may prove to be ideal pharmacological "stressor agents" during radionuclide imaging of the myocardium.

Experimental Reagents

Table 8 lists the $A_{2A}$ adenosine agonists and antagonists that were used in Example s 14–18.

| Compound | Abbreviation | Activity |
|---|---|---|
| 5'-N-ethylcarboxamidoadenosine | NECA | $A_{2A}$ agonist |
| N-[(1R)-1-methyl-1\2-phenyl-ethyl]adenosine 8-cyclopentyl-1, 3-dimethylxanthinge | R-PIA CPX | $A_{2A}$ agonist $A_{2b}$ antagonist |
| 4-[2-[[6-Amino-9-(ethyl-B-D ribofuranuron-amindosyl)-9H-purin-2-yl]aminoethyl]benz-enepropanoic acid | CGS21680 | $A_{2A}$ adenosine receptor agonist |
| N-ethyl-1'-deoxy-1'-(6-amino-2-hexynyl-9H-purin9-yl)-beta-D-ribofura nuronamide | HENECA | $A_{2a}$ adenosine receptor agonist |
| 2-alkynyladenosine | YT-0146 | $A_{2a}$ adenosine receptor agonist |
| 2-cyclohexylmethylidenehydrazino-adenosine | WRC0470 | receptor agonist |
| 4-(2-[7-amino-2-(2-furyl)[1,2,-4]triazolo[2,3-a] [1,3,5]triazin-5-ylamino]ethyl)phenol | ZM241385 | $A_{2A}$ adenosine receptor antagonist |

What we claim is:
1. A compound having the formula:

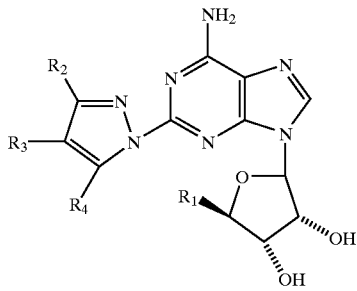

wherein $R^1 = CH_2OH$;
$R^3$ is selected from the group consisting of $CO_2R^{20}$, $-CONR^7R^8$, and aryl, wherein the aryl substituent is optionally substituted with from 1 to 3 substituents independently selected from the group consisting of halo, alkyl, and $OR^{20}$;
$R^7$ is selected from the group consisting of hydrogen, straight or branched $C_{1-15}$ alkyl and $C_{3-8}$ cycloalkyl, wherein the alkyl substituent is optionally substituted with from 1 to 3 substituents independently selected from the group consisting of aryl and $CO_2R^{20}$, and wherein the optional aryl substituent is optionally substituted with halo;
$R^8$ is selected from the group consisting of hydrogen, straight or branched $C_{115}$ alkyl and $C_{3-8}$ cycloalkyl;
$R^{20}$ is selected from the group consisting of hydrogen and $C_{1-15}$ alkyl;
and wherein $R^2$ and $R^4$ are hydrogen.
2. The compound of claim 1 wherein $R^3$ is $CO_2R^{20}$; and $R^{20}$ is selected from the group consisting of hydrogen and $C_{1-4}$ alkyl.

3. The compound of claim 1 wherein $R^3$ is $CONR^7R^8$;
$R^7$ is selected from the group consisting of hydrogen, straight or branched $C^{1-10}$ alkyl and $C_{3-5}$ cycloalkyl, wherein the alkyl substituent is optionally substituted with from 1 to 2 substituents independently selected from the group consisting of aryl and $CO_2R^{20}$;
$R^8$ is selected from the group consisting of hydrogen, straight and branched $C_{1-3}$ alkyl and $C_{3-5}$ cycloalkyl; and
$R^{20}$ is selected from the group consisting of $C_{1-4}$ alkyl.
4. The compound of claim 1 wherein $R^3$ is aryl, wherein the aryl substituent is optionally substituted with from 1 to 3 substituents independently selected from the group consisting of halo, alkyl and $OR^{20}$; and
$R^{20}$ is selected from and the group consisting of $C^{1-4}$ alkyl.
5. The compound of claim 2 wherein $R^3$ is $CO_2R^{20}$; and $R^{20}$ is selected from the group consisting of hydrogen and $C^{1-4}$ alkyl.
6. The compound of claim 3 wherein R 7 is selected from the group consisting of hydrogen, $C_{1-3}$ alkyl and cyclopentyl, wherein the alkyl substituent is optionally substituted with from 1 to 2 substituents, independently selected from the group consisting of phenyl and $CO_2R^{20}$ and wherein each optional phenyl substituent is optionally substituted with halo;
$R^8$ is selected from hydrogen and methyl; and
$R^{20}$ is selected from hydrogen and ethyl.
7. The compound of claim 4 wherein
$R^3$ is aryl, wherein the aryl substituent is phenyl optionally substituted with from 1 to 2 substituents independently selected from the group consisting of chloro, methyl and $OR^{20}$;
and $R^{20}$ is methyl.
8. The compound of claim 1 selected from the group consisting of ethyl 1-{9-[(4S,2R,3R,5R)-3,4-dihydroxy-5-(hydroxymethyl)oxolan-2-yl]-6-aminopurin-2-yl}pyrazole-4-carboxylate;
(4S,2R,3R,5R)-2-{6-amino-2-[4-(4-chlorophenyl)-pyrazolyl]purin-9-yl}-5-(hydroxymethyl)oxolane-3,4-diol;
(4S,2R,3R,5R)-2-{6-amino-2-[4-(4-methoxyphenyl) pyrazolyl]purin-9-yl}-5-(hydroxymethyl)oxolane-3,4-diol;
(4S,2R,3R,5R)-2-{6-amino-2-[4-(4-methylphenyl) pyrazolyl]purin-9-yl}-5-(hydroxymethyl)-oxolane-3,4-diol;
(1-{9-[(4S,2R,3R,5R)-3,4-dihydroxy-5-(hydroxymethyl) oxolan-2-yl]-6-aminopurin-2-yl}pyrazol-4-yl)-N-methylcarboxamide;
1-{9-[(4S,2R,3R,5R)-3,4-dihydroxy-5-(hydroxyrethyl) oxolan-2-yl]-6-aminopurin-2-yl}pyrazole-4-carboxylic acid;
(1-{9-[(4S,2R,3R,5R)-3,4-dihydroxy-5-(hydroxymethyl) oxolan-2-yl]-6-aminopurin-2-yl}pyrazol-4-yl)-N,N-dimethylcarboxamide;
(1-{9-[(4S,2R,3R,5R)-3,4-dihydroxy-5-(hydroxymethyl) oxolan-2-yl]-6-aminopurin-2-yl}pyrazol-4-yl)-N-ethylcarboxamide;
1-{9-[(4S,2R,3R,5R)-3,4-dihydroxy-5-(hydroxymethyl) oxolan-2-yl]-6-aminopurin-2-yl}pyrazole-4-carboxamide;
1-{9-[(4S,2R,3R,5R)-3,4-dihydroxy-5-(hydroxymethyl) oxolan-2-yl]-6-aminopurin-2-yl}pyrazol-$^4$-yl)-N-(cyclopentyl)carboxamide;

(1-{9-[(4S,2R,3R,5R)-3,4-dihydroxy-5-(hydroxymethyl) oxolan-2-yl]-6-aminopurin-2-yl}pyrazol-4-yl)-N-[(4-chlorophenyl)methyl]carboxamide, and ethyl 2-[(1-{9-[(4S,2R,3R,5R)-3,4-dihydroxy-5-(hydroxymethyl)oxolan-2-yl]-6-aminopurin-2-yl}pyrazol-4-yl)carbonylamino]acetate.

9. A method for stimulating coronary vasodilation in a mammal comprissing administering by intravenous bolus injection an amount of a compound of claim 1 that is sufficient to stress the heart and induce a coronary steal situation for the purposes of imaging the heart.

10. The method of claim 9 wherein the mammal is a human.

11. A pharmaceutical composition comprising a compound of claim 1 and one or mode pharmaceutical excipients.

12. The pharmaceutical composition of claim 11 wherein the pharmaceutical composition is in the form of a solution.

13. The compound of claim 8 wherein the compound is (1-{9-[(4S,2R,3R,5R)-3,4-dihydroxy-5-(hydroxymethyl) oxolan-2-yl]-6-aminopurin-2-yl}pyrazol-4-yl)-N-methylcarboxamide.

14. The compound of claim 8 wherein the compound is 1-{9-[(4S,2R,3R,5R)-3,4-dihydroxy-5-(hydroxymethyl) oxolan-2-yl]-6-aminopurin-2-yl}pyrazol-4-yl)-N-(cyclopentyl)carboxamide.

15. The compound of claim 1 wherein the compound is (1-{9-[(4S,2R,3R,5R)-3,4-dihydroxy-5(hydroxymethyl) oxolan-2-yl]-6-aminopurin-2-yl}pyrazol-4-yl)-N-ethylcarboxamide.

16. A method of dilating the coronary vessels of a mammal, as an adjunct to angioplasty, with the pharmaceutical composition of claim 11.

17. A method for adjunctive therapy in conjunction with angioplasty in a mammal comprising administering to the mammal a therapeutically effective amount of a compound of claim 1.

18. A method for inhibition of platelet aggregation in a mammal comprising administering to the mammal a therapeutically effective amount of a compound of claim 1.

* * * * *

UNITED STATES PATENT AND TRADEMARK OFFICE
CERTIFICATE OF CORRECTION

PATENT NO.      : 6,642,210 B1
DATED           : November 4, 2003
INVENTOR(S)     : Zablocki et al.

It is certified that error appears in the above-identified patent and that said Letters Patent is hereby corrected as shown below:

<u>Column 33,</u>
Line 61, delete "$C_{115}$" and replace with -- $C_{1-15}$ --.

<u>Column 34,</u>
Line 3, delete "$C^{1-10}$" and replace with -- $C_{1-10}$ --.
Lines 16 and 19, delete "$C^{1-14}$" and replace with -- $C_{1-4}$ --.
Line 20, delete "R7" and replace with -- $R^7$ --.
Line 66, delete "pyrazol-$^4$-yl)" and replace with -- pyrazole-4-yl) --.

<u>Column 35,</u>
Line 8, delete "comprissing" and replace with -- comprising --.

<u>Column 36,</u>
Line 6, delete "claim 1" and replace with -- claim 8 --.

Signed and Sealed this

Thirteenth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,642,210 B1
DATED : November 4, 2003
INVENTOR(S) : Zablocki et al.

It is certified that error appears in the above-identified patent and that said Letters Patent is hereby corrected as shown below:

Column 18,
Line 66, delete "(d, 1H), 4.34 (d, 1H), 4.64 (m, 1H), 6.06 (d, 1H), 8.38 (s," and replace with -- (d, 1H), 4.34 (d, 1H), 4.64 (m, 1H), 6.06 (d, 1H), 8.11 (s,1H), 8.38 (s, --.

Signed and Sealed this

Twenty-seventh Day of December, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,642,210 B1 | Page 1 of 1 |
| APPLICATION NO. | : 10/018446 | |
| DATED | : November 4, 2003 | |
| INVENTOR(S) | : Zablocki et al. | |

It is certified that error appears in the above-identified patent and that said Letters Patent is hereby corrected as shown below:

Figure 3
"(ml/min/mmHg,*)" should be replaced with --(ml/min/mmHg)--.

Figure 4
"ATROIVENTRICULAR" should be replaced with --ATRIOVENTRICULAR--.
"ARGONIST" should be replaced with --AGONIST--.
"msec" should be replaced with --ms--.

Column 34
Line 8, "straight and branched" should be replaced with --straight or branched--.
Line 53, "hydroxyrethyl" should be replaced with --hydroxymethyl--.

Column 35
Line 11, "purposes" should be replaced with --purpose--.
Line 15, "mode" should be replaced with --more--.

Signed and Sealed this
Eleventh Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,642,210 B1 | Page 1 of 6 |
| APPLICATION NO. | : 10/018446 | |
| DATED | : November 4, 2003 | |
| INVENTOR(S) | : Zablocki et al. | |

It is certified that error appears in the above-identified patent and that said Letters Patent is hereby corrected as shown below:

Title Page
Item (86), 371(c) date, "Apr. 12, 2000" should read --Apr. 12, 2002--.

IN THE SPECIFICATION
Column 1
Line 17, "such poor" should read --such as poor--;
Line 28, "mean" should read --means--;
Line 36, "drugs such" should read --drugs, such--;
Line 38, "A3" should read --$A_3$--;
Line 38, "in a mast" should read --in mast--;
Line 39, "give" should read --given--;
Line 42, "A-V node" should read --AV node--;
Line 46, "for the nausea" should read --for nausea--;
Line 66, "N-pyrazole" should read --N-pyrazoles--.

Column 2

Lines 7-20, " 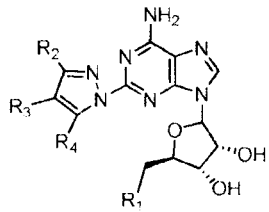 " should read -- 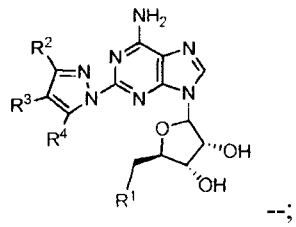 --;
Line 24, "vasodilatation" should read --vasodilation--;
Line 25, "induced" should read --and inducing a--;
Line 26, insert --.-- after heart;
Line 34, "a analog" should read --an analog--;
Line 42, "measurement" should read --measurements--;
Lines 47 and 57, "vasodialator" should read --vasodilator--;
Line 55, "A1" should read --$A_1$--.

Signed and Sealed this
Seventh Day of February, 2012

David J. Kappos
*Director of the United States Patent and Trademark Office*

Column 3

Lines 5-18, " 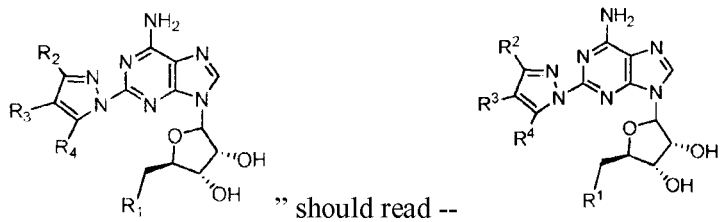 " should read -- 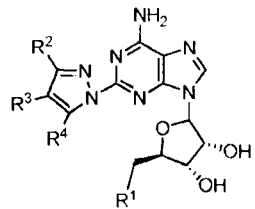 --;

Line 19, "$R^1 =CH_2OH, -CONR_5R_6$" should read --$R^1 = CH_2OH$ or $-CONR^5R^6$--;
Line 36, "$N(R_{20})_2$" should read --$N(R^{20})_2$--;
Line 41 and Lines 60-61, delete "substituted" after optional;
Line 52, "group of" should read --group consisting of--;
Line 60, "$OCON(R^2)_2$" should read --$OCON(R^{20})_2$--.

Column 4
Lines 6-7, "group of" should read --group consisting of--;
Line 10, "$N(R20)_2$" should read --$N(R^{20})_2$--;
Line 12, "$CON(R20)2$" should read --$CON(R^{20})_2$--;
Line 16 and Line 36, delete "substituted";
Line 30, "$N(R^2)_2$" should read --$N(R^{20})_2$--;
Line 31, "$SO_2NR^{20}COR_{22}$" should read --$SO_2NR^{20}COR^{22}$--;
Line 32, "$SO_2NR^{20}CO_2R^{22}$ $SO_2NR^{20}CON(R_{20})_2$" should read --$SO_2NR^{20}CO_2R^{22}$, $SO_2NR^{20}CON(R^{20})_2$--;
Lines 32-33, "$N(R^{20})_2$ $NR_{20}COR^{22}$" should read --$N(R^{20})_2$, $NR^{20}COR^{22}$--;
Line 33, "$NR^{20}CON_{20}(R^{20})_2$" should read --$NR^{20}CON(R^{20})_2$--;
Lines 44-65, should be deleted.

Column 5
Line 15, "H. $C_{1-15\ 6}$ alkyl" should read --H, $C_{1-6}$ alkyl--;
Line 26, "CF3" should read --$CF_3$--;
Line 28, "$CON(Rn_{20})_2$" should read --$CON(R^{20})_2$--;
Lines 30, 40 and 57, "$CF_3$ CN" should read --$CF_3$, CN--;
Line 31, "group of" should read --group consisting of--;
Line 32, "substituent and" should read --substituent, and--;
Line 32, delete "that";
Line 33, "CF3" should read --$CF_3$--;
Line 33, "R7" should read --$R^7$--;
Line 38, "CN, $OR^{20}$" should read --CN, and $OR^{20}$--;
Line 42, "$C_{1-4,}$ alkyl" should read --$C_{1-4}$ alkyl--;
Line 46, "group" should read --groups--;
Line 55, "O $R^{20}$" should read --and $OR^{20}$--;
Line 64, "from of hydrogen," should read --from hydrogen--;
Line 64, "hydrogen, and $C^{1-3}$ alkyl" should read --hydrogen and $C_{1-3}$ alkyl--.

CERTIFICATE OF CORRECTION (continued)

Column 6
Line 3, "in that aryl is" should read --wherein the aryl substituent is--;
Line 7, "hydrogen, and" should read --hydrogen and--;
Line 10, "$C^{1-3}$ alkyl;" should read --$C_{1-3}$ alkyl;--;
Line 11, "$C^{1-4}$ alkyl" should read --$C_{1-4}$ alkyl--;
Line 14, "$C^{1-3}$" should read --$C_{1-3}$ alkyl--;
Line 17, "ethyl1-{" should read --ethyl 1-{--.

Column 7
Line 48, "alkenyl" should read --alkynyl--.

Column 8
Line 22, "by" should read --be--;
Line 23, "hetaryl, substituted hetaryl" should read --hetaryl, or substituted hetaryl--.

Column 9
Line 21, "Heterocycyl" should read --Heterocyclyl--;
Line 32, "mono or poly substituted" should read --mono- or poly-substituted--.

Column 10

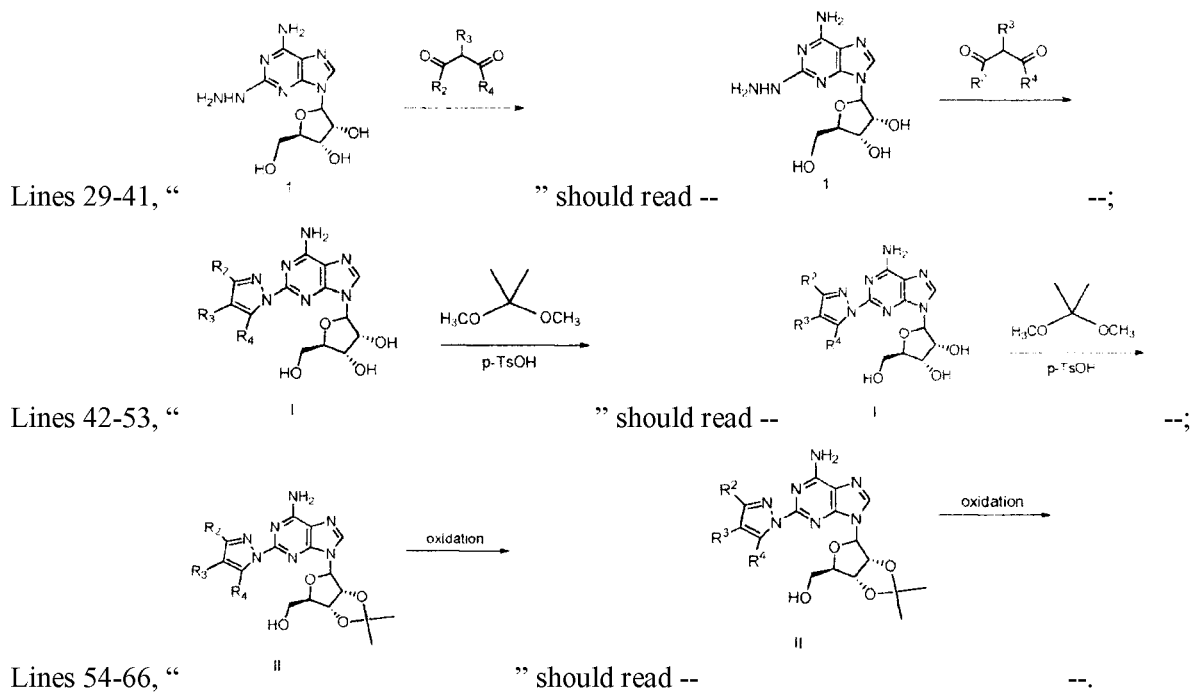

CERTIFICATE OF CORRECTION (continued)

Column 11

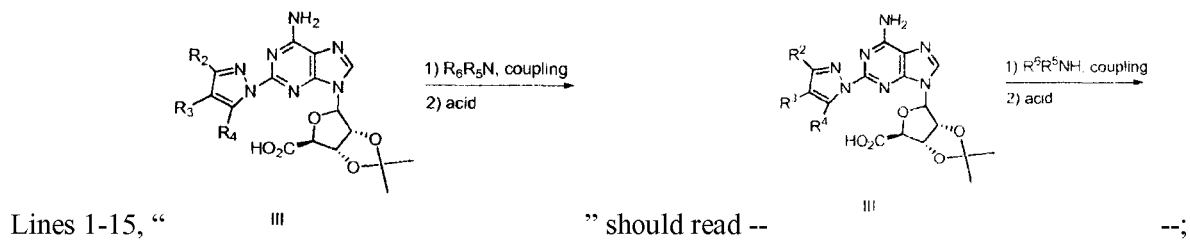

Lines 1-15, " III " should read -- III --;

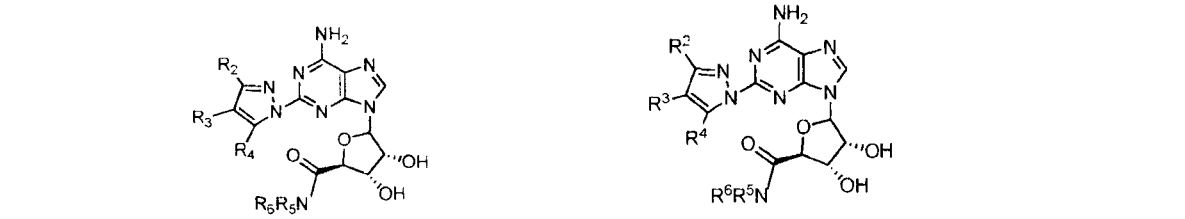

Lines 16-33, " IV " should read -- IV --;
Line 47, "HNR⁶R⁷, and compound MI" should read --HNR⁶R⁵ and compound III--;
Line 49, "²²·¹i857)" should read --22, 1857--.

Column 12

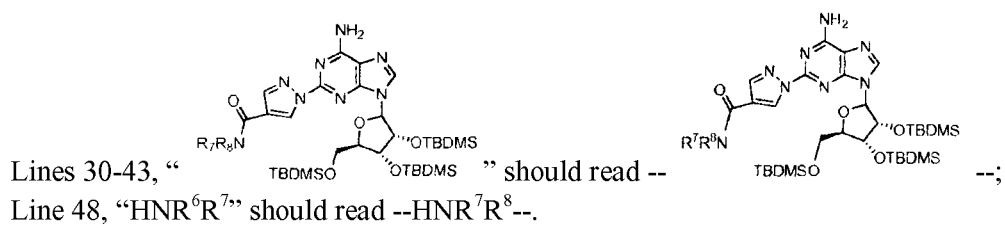

Lines 30-43, " TBDMS " should read -- TBDMSO --;
Line 48, "HNR⁶R⁷" should read --HNR⁷R⁸--.

Column 14

Line 7, "CH₃NH2" should read --CH₃NH₂--;
Line 40, "80° C." should read --80° C--;

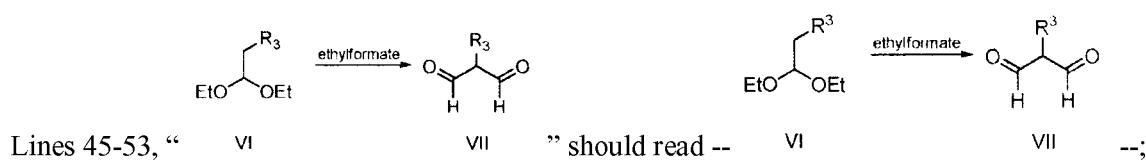

Lines 45-53, " VI VII " should read -- VI VII --;
Line 65, "A1" should read --A₁--;
Line 66, "AV-node" should read --AV node--;
Line 66, "A₂B 1A, receptors" should read --A₂B receptors--;
Line 67, "side-" should read --side--.

Column 15

Line 6, "vasodilatation" should read --vasodilation--;
Line 29, "biological" should read --biologically--;
Line 40, "proteinase" should read --proteinases--;
Line 46, "agents" should read --agent--.

Column 16
Line 63, "Ethyl1-{" should read --Ethyl 1-{--.

Column 17
Line 1, "((0.019 g, 0.12 mmol)" should read --(0.019 g, 0.12 mmol)--;
Line 2, "heated heated" should read --heated--;
Lines 2, 32, and 62, "80° C. for" should read --80° C for--;
Line 25, "(4S,2R,3R,5R)-2-{Amino" should read --(4S,2R,3R,5R)-2-{6-Amino--.

Column 18
Line 28, "80° C. for" should read --80° C for--;
Line 62, "(40% sol. In water)" should read --(40% sol. in water)--;
Lines 62-63, "heated at 65° C. in for" should read --was heated at 65° C for--.

Column 19
Line 18, "Acid" should read --acid--;
Line 23, "Δ3.75" should read --δ 3.75--.

Column 20
Line 46, "80° C. for" should read --80° C for--;
Line 50, "2 m L1N" should read --2 mL 1N--;
Line 51, "for 72." should read --for 72 h.--.

Column 21
Line 41, "{9-(4S" should read --{9-[(4S--;
Line 43, "carbonylaminolacetate" should read --carbonylamino]acetate--;
Line 52, "teated" should read --treated--;
Line 60, "23> C. for" should read --23° C for--;
Line 66, "Ki.'s" should read --Ki's--.

Column 22
Line 26, "$A_{2B\ and A3}AdoRs$" should read --$A_{2B}$ and $A_3$AdoRs--;
Lines 37-38, "Parlinson's" should read --Parkinson's--.

Column 24
Line 31, "potency Compound" should read --potency of Compound--;
Line 33, "$A_{2A}$ doR" should read --$A_{2A}$ AdoR--.

Column 25
Line 4, "rinse" should read --rinsed--.

Column 27
Line 1, "rinse" should read --rinsed--.

CERTIFICATE OF CORRECTION (continued)

U.S. Pat. No. 6,642,210 B1

Column 28
Line 67, "rinse" should read --rinsed--.

Column 29
Line 6, "95% $_2$" should read --95% $O_2$--;
Line 44, "100% 02" should read --100% $O_2$--;
Lines 44-45, "of $_2$ in" should read --of $O_2$ in--.

Column 32
Line 33, "$t_{0.5}$." should read --$t_{0.5}$--.

Column 33

Claim 1, lines 34-45, " 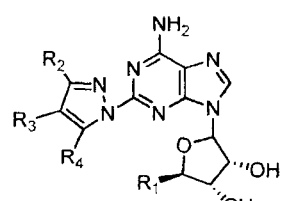 " should read -- 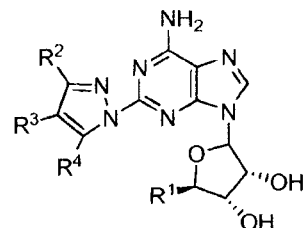 --.

UNITED STATES PATENT AND TRADEMARK OFFICE
CERTIFICATE OF CORRECTION

PATENT NO. : 6,642,210 B1
APPLICATION NO. : 10/018446
DATED : November 4, 2003
INVENTOR(S) : Zablocki et al.

It is certified that error appears in the above-identified patent and that said Letters Patent is hereby corrected as shown below:

Title Page
Item (86), 371(c) date, "Apr. 12, 2000" should read --Apr. 12, 2002--.

IN THE SPECIFICATION
Column 1
Line 17, "such poor" should read --such as poor--;
Line 28, "mean" should read --means--;
Line 36, "drugs such" should read --drugs, such--;
Line 38, "A3" should read --$A_3$--;
Line 38, "in a mast" should read --in mast--;
Line 39, "give" should read --given--;
Line 42, "A-V node" should read --AV node--;
Line 46, "for the nausea" should read --for nausea--;
Line 66, "N-pyrazole" should read --N-pyrazoles--.

Column 2

Lines 7-20, " " should read -- 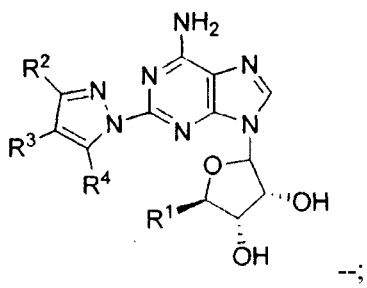 --;
Line 24, "vasodilatation" should read --vasodilation--;
Line 25, "induced" should read --and inducing a--;
Line 26, insert --.-- after heart;
Line 34, "a analog" should read --an analog--;

This certificate supersedes the Certificate of Correction issued February 17, 2012.

Signed and Sealed this
Tenth Day of April, 2012

David J. Kappos
*Director of the United States Patent and Trademark Office*

CERTIFICATE OF CORRECTION (continued)
U.S. Pat. No. 6,642,210 B1

Line 42, "measurement" should read --measurements--;
Lines 47 and 57, "vasodialator" should read --vasodilator--;
Line 55, "A1" should read --$A_1$--.

Column 3

Lines 5-18, " " should read -- 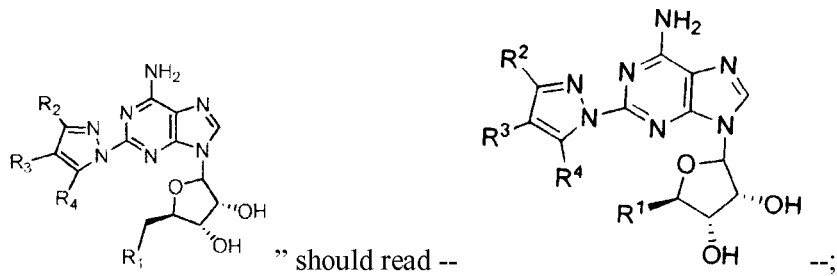 --;
Line 19, "$R^1$ =$CH_2OH$, -$CONR_5R_6$" should read --$R^1$ = $CH_2OH$ or -$CONR^5R^6$--;
Line 36, "$N(R_{20})_2$" should read --$N(R^{20})_2$--;
Line 41 and Lines 60-61, delete "substituted" after optional;
Line 52, "group of" should read --group consisting of--;
Line 60, "$OCON(R^2)_2$" should read --$OCON(R^{20})_2$--.

Column 4
Lines 6-7, "group of" should read --group consisting of--;
Line 10, "$N(R20)_2$" should read --$N(R^{20})_2$--;
Line 12, "$^{CON(R20)}$)2" should read --$CON(R^{20})_2$--;
Line 16 and Line 36, delete "substituted";
Line 30, "$N(R^2)_2$" should read --$N(R^{20})_2$--;
Line 31, "$SO_2NR^{20}COR_{22}$" should read --$SO_2NR^{20}COR^{22}$--;
Line 32, "$SO_2NR^{20}CO_2R^{22}$ $SO_2NR^{20}CON(R_{20})_2$" should read --$SO_2NR^{20}CO_2R^{22}$, $SO_2NR^{20}CON(R^{20})_2$--;
Lines 32-33, "$N(R^{20})_2$ $NR_{20}COR^{22}$" should read --$N(R^{20})_2$, $NR^{20}COR^{22}$--;
Line 33, "$NR^{20}CON_{20}(R^{20})_2$" should read --$NR^{20}CON(R^{20})_2$--;
Lines 44-65, should be deleted.

Column 5
Line 15, "H. $C_{1-15\ 6}$ alkyl" should read --H, $C_{1-6}$ alkyl--;
Line 26, "CF3" should read --$CF_3$--;
Line 28, "$CON(Rn_{20})_2$" should read --$CON(R^{20})_2$--;
Lines 30, 40 and 57, "$CF_3$ CN" should read --$CF_3$, CN--;
Line 31, "group of" should read --group consisting of--;
Line 32, "substituent and" should read --substituent, and--;
Line 32, delete "that";
Line 33, "CF3" should read --$CF_3$--;
Line 33, "R7" should read --$R^7$--;
Line 38, "CN, $OR^{20}$" should read --CN, and $OR^{20}$--;
Line 42, "$C_{1-4}$, alkyl" should read --$C_{1-4}$ alkyl--;
Line 46, "group" should read --groups--;
Line 55, "O $R^{20}$" should read --and $OR^{20}$--;

Line 64, "from of hydrogen," should read --from hydrogen--;
Line 64, "hydrogen, and $C^{1-3}$ alkyl" should read --hydrogen and $C_{1-3}$ alkyl--.

Column 6
Line 3, "in that aryl is" should read --wherein the aryl substituent is--;
Line 7, "hydrogen, and" should read --hydrogen and--;
Line 10, "$C^{1-3}$ alkyl;" should read --$C_{1-3}$ alkyl;--;
Line 11, "$C^{1-4}$ alkyl" should read --$C_{1-4}$ alkyl--;
Line 14, "$C^{1-3}$" should read --$C_{1-3}$ alkyl--;
Line 17, "ethyl1-{" should read --ethyl 1-{--.

Column 7
Line 48, "alkenyl" should read --alkynyl--.

Column 8
Line 22, "by" should read --be--;
Line 23, "hetaryl, substituted hetaryl" should read --hetaryl, or substituted hetaryl--.

Column 9
Line 21, "Heterocycyl" should read --Heterocyclyl--;
Line 32, "mono or poly substituted" should read --mono- or poly-substituted--.

Column 10

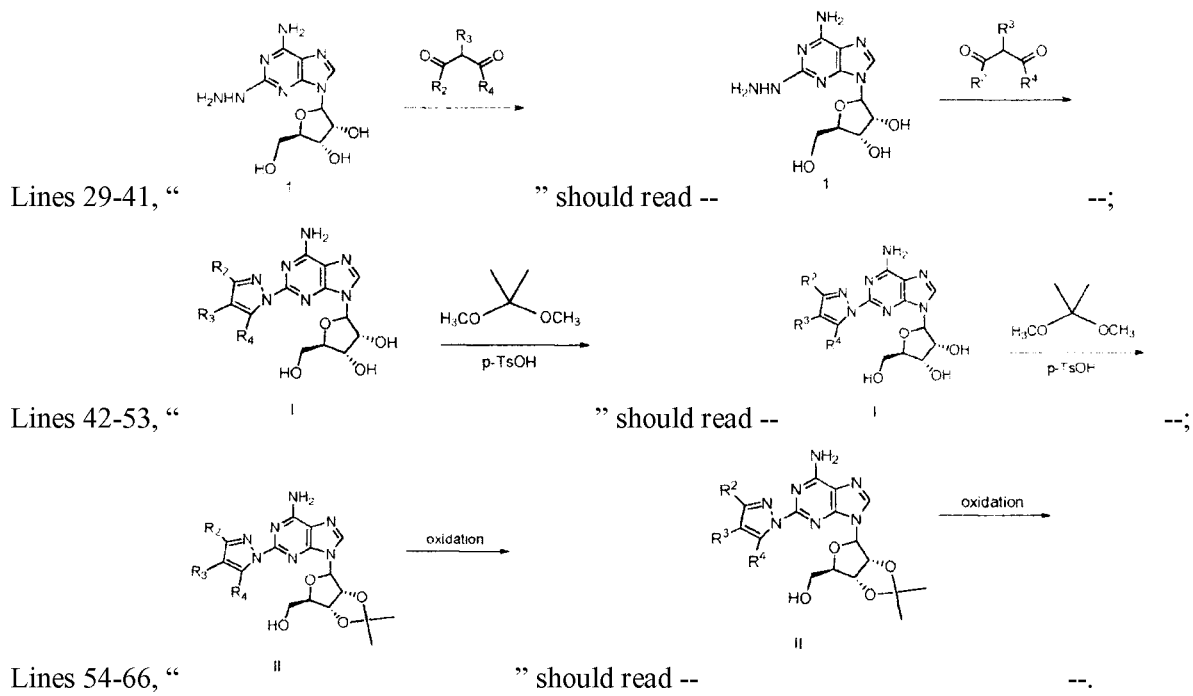

Lines 29-41, " " should read -- --;

Lines 42-53, " " should read -- --;

Lines 54-66, " " should read -- --.

Column 11

Lines 1-15, " 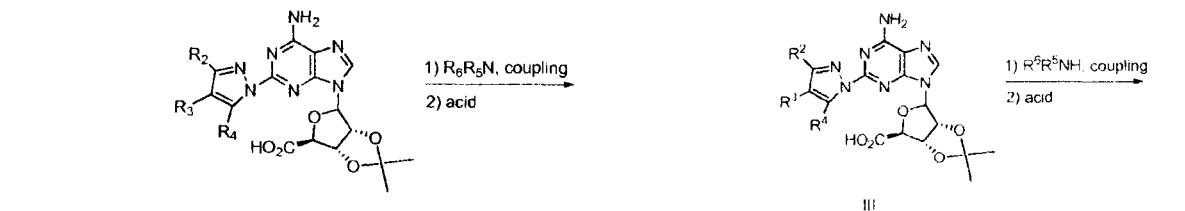 ";

Lines 16-33, " 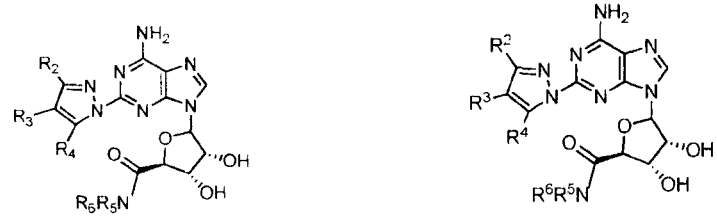 ";

Line 47, "HNR⁶R⁷, and compound MI" should read --HNR⁶R⁵ and compound III--;
Line 49, "²²·¹i857)" should read --22, 1857--.

Column 12

Lines 30-43, " 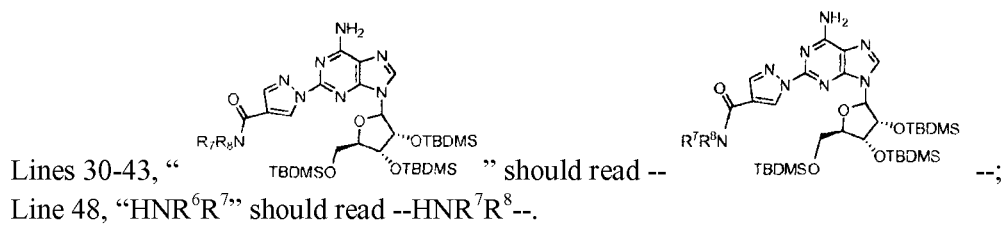 ";
Line 48, "HNR⁶R⁷" should read --HNR⁷R⁸--.

Column 14
Line 7, "CH₃NH2" should read --CH₃NH₂--;
Line 40, "80° C." should read --80° C--;

Lines 45-53, "  ";
Line 65, "A1" should read --A₁--;
Line 66, "AV-node" should read --AV node--;
Line 66, "A₂B 1A, receptors" should read --A₂ᴮ receptors--;
Line 67, "side-" should read --side--.

Column 15
Line 6, "vasodilatation" should read --vasodilation--;
Line 29, "biological" should read --biologically--;
Line 40, "proteinase" should read --proteinases--;
Line 46, "agents" should read --agent--.

Column 16
Line 63, "Ethyl1-{" should read --Ethyl 1-{--.

Column 17
Line 1, "((0.019 g, 0.12 mmol)" should read --(0.019 g, 0.12 mmol)--;
Line 2, "heated heated" should read --heated--;
Lines 2, 32, and 62, "80° C. for" should read --80° C for--;
Line 25, "(4S,2R,3R,5R)-2-{Amino" should read --(4S,2R,3R,5R)-2-{6-Amino--.

Column 18
Line 28, "80° C. for" should read --80° C for--;
Line 62, "(40% sol. In water)" should read --(40% sol. in water)--;
Lines 62-63, "heated at 65° C. in for" should read --was heated at 65° C for--.

Column 19
Line 18, "Acid" should read --acid--;
Line 23, "Δ3.75" should read --δ 3.75--.

Column 20
Line 46, "80° C. for" should read --80° C for--;
Line 50, "2 m L1N" should read --2 mL 1N--;
Line 51, "for 72." should read --for 72 h.--.

Column 21
Line 41, "{9-(4S" should read --{9-[(4S--;
Line 43, "carbonylaminolacetate" should read --carbonylamino]acetate--;
Line 52, "teated" should read --treated--;
Line 60, "23> C. for" should read --23° C for--;
Line 66, "Ki.'s" should read --Ki's--.

Column 22
Line 26, "$A_{2B\ andA3}$AdoRs" should read --$A_{2B}$ and $A_3$AdoRs--;
Lines 37-38, "Parlinson's" should read --Parkinson's--.

Column 24
Line 31, "potency Compound" should read --potency of Compound--;
Line 33, "$A_{2A}$ doR" should read --$A_{2A}$ AdoR--.

Column 25
Line 4, "rinse" should read --rinsed--.

Column 27
Line 1, "rinse" should read --rinsed--.

CERTIFICATE OF CORRECTION (continued)

Column 28
Line 67, "rinse" should read --rinsed--.

Column 29
Line 6, "95% $_2$" should read --95% $O_2$--;
Line 44, "100% 02" should read --100% $O_2$--;
Lines 44-45, "of $_2$ in" should read --of $O_2$ in--.

Column 32
Line 33, "$t_{0.5}$-" should read --$t_{0.5}$--.

Column 33

Claim 1, lines 34-45, " 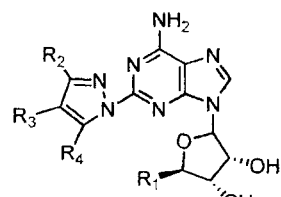 " should read -- 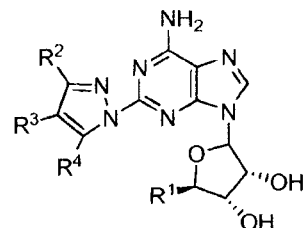 --.

UNITED STATES PATENT AND TRADEMARK OFFICE
Certificate

Patent No. 6,642,210 B1

Patented: November 4, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jeff A. Zablocki, Mountain View, CA (US); Elfatih O. Elzein, Freemont, CA (US); Venkata P. Palle, Sunnyvale, CA (US); and Luiz Belardinelli, Palo Alto, CA (US).

Signed and Sealed this Eleventh Day of June 2013.

SHAOJIA ANNA JIANG
*Supervisory Patent Examiner*
Art Unit 1623
Technology Center 1600